US009127164B2

(12) United States Patent
Ramage et al.

(10) Patent No.: US 9,127,164 B2
(45) Date of Patent: Sep. 8, 2015

(54) FLUORESCENT DYES AND USES THEREOF

(75) Inventors: Robert Ramage, Edinburgh (GB); Beatrice Maltman, Midlothian (GB); Graham Cotton, Edinburgh (GB); Sarah Claire Monique Couturier, Merouville (FR); Robert Austin Simms McMordie, Moira (IE)

(73) Assignee: ALMAC SCIENCES (SCOTLAND) LIMITED, Edinburgh (GB)

( * ) Notice: Subject to any disclaimer, the term of this patent is extended or adjusted under 35 U.S.C. 154(b) by 1582 days.

(21) Appl. No.: 12/091,792

(22) PCT Filed: Oct. 27, 2006

(86) PCT No.: PCT/GB2006/004015
§ 371 (c)(1),
(2), (4) Date: Sep. 3, 2008

(87) PCT Pub. No.: WO2007/049057
PCT Pub. Date: May 3, 2007

(65) Prior Publication Data
US 2009/0226940 A1  Sep. 10, 2009

(30) Foreign Application Priority Data

Oct. 28, 2005 (GB) .................................. 0522029.8
Jul. 5, 2006 (GB) .................................. 0613334.2

(51) Int. Cl.
*G01N 33/533* (2006.01)
*G01N 21/76* (2006.01)
*C09B 15/00* (2006.01)
*G01N 33/58* (2006.01)

(52) U.S. Cl.
CPC .............. *C09B 15/00* (2013.01); *G01N 33/533* (2013.01); *G01N 33/582* (2013.01); *Y10T 436/145555* (2015.01)

(58) Field of Classification Search
CPC . G01N 33/542; G01N 33/582; G01N 33/533; C09B 15/00; C07D 219/10
See application file for complete search history.

(56) References Cited

FOREIGN PATENT DOCUMENTS

| EP | 0533200 A1 | 3/1993 |
|---|---|---|
| WO | WO 01/40218 | 6/2001 |
| WO | WO 02/081509 | 10/2002 |
| WO | WO 02/099424 | 12/2002 |
| WO | WO 03/089663 | 10/2003 |
| WO | WO 03/089665 | 10/2003 |

OTHER PUBLICATIONS

Wakelin, L. et al., J. Med. Chem. 1987, vol. 30, pp. 855-861.*
Mayer, A. et al., "Luminescent Labels—More than Just an Alternative to Radioisotopes?", Angew. Chem. Int. Ed. Engl., 1994, 33, pp. 1044-1072.
Chemical Abstracts, vol. 38, abs No. 357e-i, 358a-e, 1 page (1944).
Chemical Abstracts, vol. 41, abs No. 458c-i, 459a-f, 2 pages (1947).
Chemical Abstracts, vol. 44, abs No. 633i, 634a-g, 1 page (1950).
Schwarz et al., "Selected aminoacridines as fluorescent probes in cytochemistry in general and in the detection of cancer cells in particular", Analytical and Quantitative Cytology, vol. 41, No. 1, 1982, pp. 44-54.
Abraham et al.,: "Covalent labeling of specific membrane carbohydrate residues with fluorescent probes", Biochimica et Biophysica Acta, vol. 597, No. 2, 1980, pp. 285-291.
Szymanska et al., "Synthesis and photophysics of acridine derivatives", Chemicstry of Heterocyclic Compounds, vol. 36, No. 7, 2001, pp. 801-808.
Database: Beilstein Institute for Organic Chemistry, Frankfurt-Main, DE; Database accession No. BRN 207524, 1949.
Database: Caplus [Online], Chemical Abstracts Service, Columbus,Ohio, US; Tomosaka, Hideyuki et al: "Proposed two-molecule intercalation between neighboring base pairs of DNA", Database accession No. 1995:609850,Bioscience, Biotechnology & Biochemistry, vol. 59, No. 5, 1995, p. 960-961.
Wakelin et al., "Relationships between DNA-Binding Kinetics and Biological Activity for the 9-Aminoacridine-4-carboxamide Class of Antitumor Agents", J. Med. Chem., vol. 30, No. 5, 1987, pp. 855-861.
Denny et al., "Potential Antitumor Agents. 49. 5-Substituted Derivatives of N-[2-(Dimethylamino)ethyl ]-9-aminoacridi ne-4-carboxamide with in Vivo Solid-Tumor Activity", J. Med. Chem., vol. 30, No. 4, 1987, pp. 658-663.
Database: Beilstein Institute for Organic Chemistry, Frankfurt-Main, DE; Wilkinson; Finar: J. Chem. Soc., 1947, pp. 759-761, Database accession No. BRN 171909.
Database: Beilstein Institute for Organic Chemistry, Frankfurt-Main, DE; Goldberg; Kelly: J. Chem. Soc. , 1947, pp. 637-640, Database accession No. BRN 193349.
Database: Beilstein Institute for Organic Chemistry, Frankfurt-Main, DE; Albert, Gledhill: J. Soc. Chem. Ind., 1945, pp. 169-170, Database accession No. BRN 207381.
Database: Beilstein Institute for Organic Chemistry, Frankfurt-Main, DE; Matsumura: J . Am. Chem. Soc . , vol. 57, 1935, pp. 1533-1535, Database accession No. BRN 258292.
Database: Beilstein Institute for Organic Chemistry, Frankfurt-Main, DE; R. M. Acheson et al.: Chem. Res. Miniprint, 1983, pp. 0101-0132, Database accession No. BRN 6529455, 6525629, 6523231, 6551525, 6549602.
Database: Beilstein Institute for Organic Chemistry, Frankfurt-Main, DE; Goldberg, Kelly: J. Chem. Soc. , 1946, pp. 102-107, Database accession No. BRN 24431.
Database: Beilstein Institute for Organic Chemistry, Frankfurt-Main, DE; Albert,-Ritchie: J. Chem. Soc., 1943, pp. 458-460, Database accession No. BRN 173190.
Database: Beilstein Institute for Organic Chemistry, Frankfurt-Main, DE ; DE 393 411 C (Hoechster Farbw. ) 4 Apr. 1, 1924, Database accession No. BRN 171920.

* cited by examiner

*Primary Examiner* — Shafiqul Haq
(74) *Attorney, Agent, or Firm* — Hoxie & Associates LLC

(57) ABSTRACT

The present invention relates to fluorescent dyes based on acridine derivatives and use of such dyes, for example, in biochemical and/or cell based assays. A preferred feature of some of the dyes described is their long fluorescence lifetimes and their use to label biological molecules.

28 Claims, 8 Drawing Sheets

Emission spectrum

Excitation scan

500nM in PBS, Ex 405nm, 1 scan

500nM in PBS, Ex 405nm, 1 scan

500nM in PBS, Ex 405nm, 1 scan

FLUORESCENT DYES AND USES THEREOF

FIELD OF THE INVENTION

The present invention relates to fluorescent dyes based on acridine derivatives and use of such dyes, for example, in biochemical and/or cell based assays. A preferred feature of some of the dyes described is their long fluorescence lifetimes and their use to label biological molecules

BACKGROUND TO THE INVENTION

Fluorescent molecules, including dyes have long been used as agents for labelling and detecting biological molecules in cell-free biochemical assays, as well as cell based assays. However, in many systems, there is a background fluorescence and it is necessary to have a good signal-to-noise ratio in order to successfully detect the relevant fluorescent signal.

Many highly fluorescent dyes are known and used in order to improve signal-to-noise ratio. An alternative method is to employ fluorescent molecules which display a fluorescence lifetime significantly different to the system being studied such that detection of the fluorescent molecule can easily be discerned from background.

There is always a need for new fluorescent molecules and/or identification of known molecules which possess the appropriate fluorescent properties for use in biochemical and cell based assays and it is amongst the objects of the present invention to provide and/or identify new fluorescent molecules for use in such assays, as well as the use of the fluorescent molecules in such assays.

SUMMARY OF THE INVENTION

Thus, in a first aspect, there is provided use of a reagent for fluorescent labelling and/or lifetime detection of a target material, wherein said reagent comprises a fluorescent dye of the formula (I):

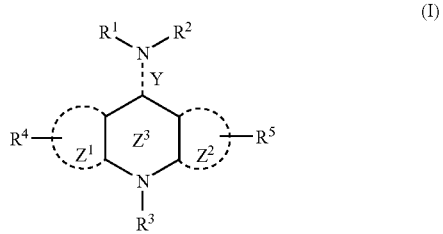

(I)

wherein:

the dashed line Y is a single or double bond; when the dashed line Y is a single bond, the ring $Z^3$ is a pyridyl or dihydropyridyl ring; when the dashed line is a double bond, the ring $Z^3$ is a dihydropyridyl ring, and optionally one of $R^1$ and $R^2$ may be absent, provided that when both $R^1$ and $R^2$ are present the nitrogen atom to which they are attached is positively charged;

group $R^4$ is attached to an available atom of the $Z^1$ ring structure and group $R^5$ is attached to an available atom of the $Z^2$ ring structure;

$Z^1$ and $Z^2$ independently represent the atoms necessary to complete one ring, two fused rings, or three fused rings or aromatic or heteroaromatic ring systems, each ring independently having five or six atoms independently selected from carbon atoms and optionally no more than two atoms independently selected from oxygen, nitrogen and sulphur;

$R^1$, $R^2$, $R^3$ are independently each occurrence selected from hydrogen, halogen, amide, hydroxyl, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, and quaternary ammonium.

$R^4$ and $R^5$ are independently at each occurrence selected from hydrogen, halogen, amide, hydroxyl, cyano, nitro, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, quaternary ammonium and the group -J, —K, or -J-K; wherein J is a linker group and K is a target bonding group with the proviso that at least one occurrence of $R^4$ and/or $R^5$ is not hydrogen;

and wherein when the ring $Z^3$ is a pyridyl ring, $R^3$ may optionally be absent, provided that when $R^3$ is present, the nitrogen atom to which it is attached is positively charged;

or when the dashed line Y is a single bond, $R^1$ and $R^2$ together with the nitrogen atom to which they are bonded may form the group

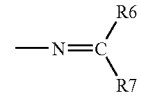

wherein $R^6$ and $R^7$ have the same meaning as given for $R^1$, $R^2$ and $R^3$ including salts of formula (I).

The dyes according to the present invention are particularly suitable for use as fluorescence lifetime dyes. In accordance with the present invention, the term lifetime dye is intended to mean a dye having a measurable fluorescence lifetime, defined as the average amount of time that the dye remains in its excited state following excitation (Lackowicz, J. R., Principles of Fluorescence Spectroscopy, Kluwer Academic/Plenum Publishers, New York, (1999)).

Preferably, the fluorescent dye has a fluorescence lifetime in the range from 5-30 nanoseconds, preferably 8-25 nanoseconds more preferably from 12-25 nanoseconds.

Preferably, $Z^1$ and $Z^2$ independently form an aromatic ring, or fused aromatic rings. The aromatic ring(s) may be substituted or unsubstituted. Preferably, the aromatic ring is a substituted or unsubstituted phenyl group (which may be referred to herein as a benzene ring).

Preferably, fused aromatic rings form a group selected from naphthyl, phenanthryl or anthracyl (which may be referred to herein as naphthalene, phenanthrene or anthracene rings respectively).

Unsubstituted or substituted aryl is an aromatic substituent containing one or two fused aromatic rings containing 6 to 10 carbon atoms, for example phenyl or naphthyl, the aryl being optionally and independently substituted by one or more substituents, for example halogen, hydroxyl, straight or branched chain $C_1$-$C_6$ alkyl, aralkyl or alkoxy groups.

Heteroaryl is a mono- or bicyclic 5 to 10 membered aromatic ring system containing at least one and no more than 3 heteroatoms which may be selected from N, O and S and is optionally and independently substituted by one or more substituents, for example halogen, hydroxyl, straight or branched chain $C_1$-$C_6$ alkyl, aralkyl or alkoxy groups.

Aralkyl is typically a $C_1$-$C_6$ alkyl group substituted by an aryl or heteroaryl group.

Typically the substituted or unsubstituted alkyl or alkenyl is $C_1$-$C_6$ alkyl or alkenyl, with substituents understood to include amino, hydroxy, sulphydryl, carbonyl and phosphate groups.

Preferably, at least one of groups $R^1$, $R^2$, $R^3$, $R^4$ and $R^5$ in the dye of formula (I) is the group -J, —K or -J-K. More preferably Y is a single bond, and $Z^3$ is a pyridyl ring $R^1$, $R^2$, are H, $R^3$ is absent and $R^4$ and/or $R^5$ in at least one occurrence is the groups -J, —K or -J-K.

Suitable linker groups J may contain 1-40 (especially 1-10) chain atoms comprising carbon, and optionally nitrogen, oxygen, sulphur and/or phosphorus. For example, the chain may be a substituted or unsubstituted alkyl, alkenyl, alkyoxy chain, alkanecarboxamido, such as acetamido.

Suitably, the biological molecule bonding group K is a reactive or functional group. A reactive group of a compound according to formula (I) can react under suitable conditions with a functional group of a biological molecule; a functional group of a compound according to formula (I) can react under suitable conditions with a reactive group of the biological molecule such that the biological molecule becomes labelled with the compound.

Preferably, when K is a reactive group, it is selected from succinimidyl ester, sulpho-succinimidyl ester, isothiocyanate, maleimide, haloacetamide, acid halide, vinylsulphone, dichlorotriazine, carbodimide, hydrazide and phosphoramidite pentafluoro phenylester and alkylhalide. Preferably, when K is a functional group, it is selected from hydroxy, amino, sulphydryl, imidazole, carboxyl, carbonyl including aldehyde and ketone, phosphate and thiophosphate. It is understood that when K is a functional group, it may become modified when conjugating to the biological molecule, for example an amino group may become an amide, or a carboxyl may become ester. By virtue of these reactive and functional groups the compounds of formula (I) may be reacted with and covalently bound to biological molecules.

The skilled addressee readily knows which functional/reactive groups are capable of reacting with corresponding reactive/functional groups of the biological molecule to which the dye is to be coupled.

Conveniently, at least one of the groups $R^1$, $R^2$, $R^3$, $R^4$ and $R^5$ of the dyes of formula (I) may be a water solubilising group for conferring a hydrophilic characteristic to the compound. Solubilising groups, for example, sulphonate, sulphonic acid and quaternary ammonium, may be attached directly to the aromatic ring structures $Z^1$ and/or $Z^2$ of the compound of formula (I). Alternatively, solubilising groups may be attached by means of a linker, such as $C_1$-$C_6$ alkyl linker chain to said ring structures and may be, for example, selected from the group —$(CH_2—)_n$M where M is selected from sulphonate, sulphate, phosphonate, phosphate, quaternary ammonium and carboxyl; and n is an integer from 1 to 6. Alternative solubilising groups may be carbohydrate residues, for example, monosaccharides. Examples of water solubilising constituents include $C_1$-$C_6$ alkyl sulphonates, such as —$(CH_2)_3$—$SO_3^-$ and —$(CH_2)_4$—$SO_3^-$. However, one or more sulphonate or sulphonic acid groups attached directly to the aromatic ring structures of a dye of formula (I) are particularly preferred. Water solubility may be advantageous when labelling proteins.

As will be appreciated some of the fluorescent dyes of the present invention may contain a charge, for example, at a quaternary amino group, and this may be used to form salts or to bind negatively charged molecules such as DNA and/or RNA.

Suitable biological molecules include, but are not limited to the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, hormones, cells, cell membranes and toxins.

In a further aspect, there is provided a fluorescent dye-biological molecule conjugate, for use in a biological assay comprising a dye of the formula (I) conjugated to a biological molecule:

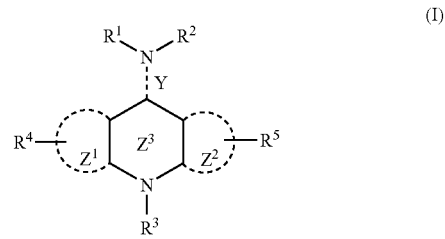

wherein:

the dashed line Y is a single or double bond when the dashed line Y is a single bond, the ring $Z^3$ is a pyridyl or dihydropyridyl ring; when the dashed line is a double bond, the ring $Z^3$ is a dihydropyridyl ring, and optionally one of $R^1$ and $R^2$ may be absent, provided that when both $R^1$ and $R^2$ are present the nitrogen atom to which they are attached is positively charged;

group $R^4$ is attached to an available atom of the $Z^1$ ring structure and group $R^5$ is attached to an available atom of the $Z^2$ ring structure;

$Z^1$ and $Z^2$ independently represent the atoms necessary to complete one ring, two fused rings, or three fused rings or aromatic or heteroaromatic ring systems, each ring having five or six atoms independently selected from carbon atoms and optionally no more than two atoms independently selected from oxygen, nitrogen and sulphur;

wherein at least one of said groups $R^4$ and $R^5$ are independently a linker group -J (as herein before defined) conjugated to a biological molecule;

and wherein any of said $R^1$, $R^2$ or $R^3$ are independently at each occurrence selected from hydrogen, halogen, amide, hydroxyl, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, quaternary ammonium;

and wherein any of said remaining $R^4$ and $R^5$ are independently at each occurrence selected from hydrogen, halogen, amide, hydroxyl, cyano, nitro, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, quaternary ammonium;

and wherein when the ring $Z^3$ is a pyridyl ring, $R^3$ may optionally be absent, provided that when $R^3$ is present, the nitrogen atom to which it is attached is positively charged;

or when the dashed line Y is a single bond, $R^1$ and $R^2$ together with the nitrogen atom to which they are bonded form the group

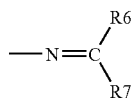

wherein $R^6$ and $R^7$ have the same meaning as given for $R^1$, $R^2$ and $R^3$; including salts of formula (I).

The dyes and dye-conjugates described herein may additionally comprise a cell entry peptide. The cell entry peptide may be Penetratin (Cyclacel, UK), for example TAT or Chariot.

In a yet further aspect, there is provided a fluorescent dye of the formula (I):

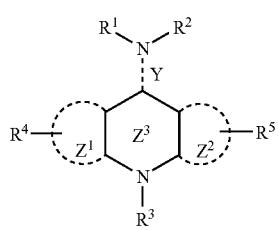

wherein:
the dashed line Y is a single or double bond; when the dashed line Y is a single bond, the ring $Z^3$ is a pyridyl or dihydropyridyl ring; when the dashed line is a double bond, the ring $Z^3$ is a dihydropyridyl ring, and optionally one of $R^1$ and $R^2$ may be absent, provided that when both $R^1$ and $R^2$ are present the nitrogen atom to which they are attached is positively charged;
group $R^4$ is attached to an available atom of the $Z^1$ ring structure and group $R^5$ is attached to an available atom of the $Z^2$ ring structure;
$Z^1$ and $Z^2$ independently represent the atoms necessary to complete one ring, two fused rings, or three fused rings or aromatic or heteroaromatic ring systems, each ring having five or six atoms independently selected from carbon atoms and optionally no more than two atoms independently selected from oxygen, nitrogen and sulphur;
wherein at least one of said groups $R^4$ and $R^5$ are independently -J or -J-K conjugated to a biological molecule, wherein J is a linker group and K is a target bonding group;
and wherein any of said $R^1$, $R^2$ and $R^3$ are independently at each occurrence selected from hydrogen, halogen, amide, hydroxyl, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, and quaternary ammonium;
and wherein any of said remaining $R^4$ and $R^5$ are independently at each occurrence selected from hydrogen, halogen, amide, hydroxyl, cyano, nitro, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, and quaternary ammonium;

and wherein when the ring $Z^3$ is a pyridyl ring, $R^3$ may optionally be absent,
provided that when $R^3$ is present, the nitrogen atom to which it is attached is positively charged;
or when the dashed line Y is a single bond, $R^1$ and $R^2$ together with the nitrogen atom to which they are bonded form the group

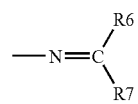

wherein $R^6$ and $R^7$ have the same meaning as given for either $R^1$, $R^2$ and $R^3$; including salts of formula (I).

Preferred substituents are described above with reference to the first aspect.

Particularly preferred are dyes having the formulae (II) or (III) shown below and having the same definitions as described hereinabove.

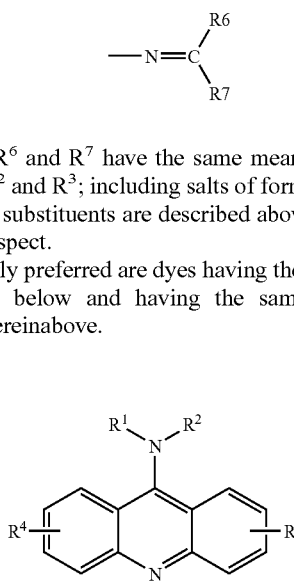

Further preferred dyes in accordance with the present invention are according to formula (Iv):

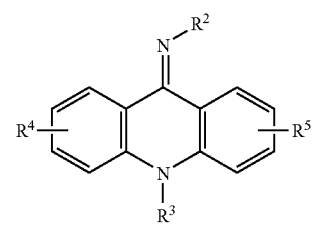

wherein at least one of said $R^4$ or $R^5$ is independently -J, —K, or -JK wherein J is a linker group and K is a target bonding group, as hereinbefore described. Preferred linker groups J may contain 1-10 chain atoms comprising carbon and optionally nitrogen, e.g. substituted or unsubstituted alkyl or alkanecarboxamido; and K is a reactive or functional group, such as a succininidyl ester, sulphydryl, hydroxyl, carboxyl, amino or the like.

Exemplary routes for the synthesis of some of the dyes according to the present invention are as follows:

Synthesis of 9-aminoacridine Derivatives with Ring Substituents

Method 1

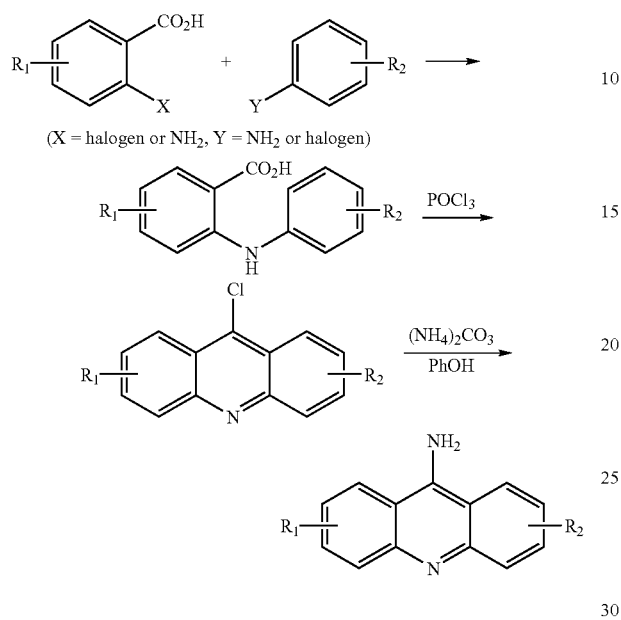

Method 2

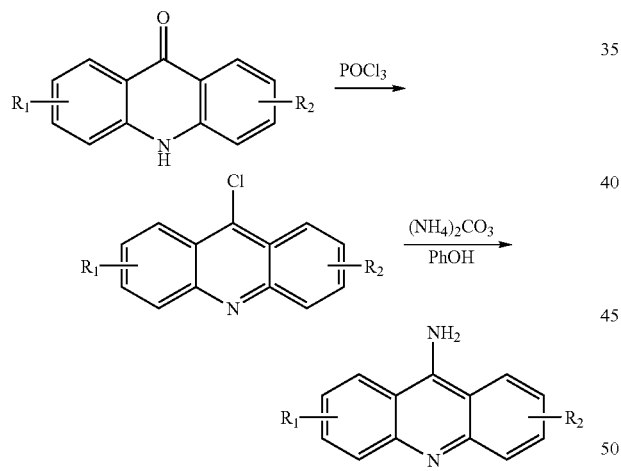

The synthesis of a variety of ring substituted acridones have been reported, which can then be converted into the corresponding 9-aminoacridine derivative using the above synthetic procedures.

Derivatives of the 9-amino functionality:

Method 3

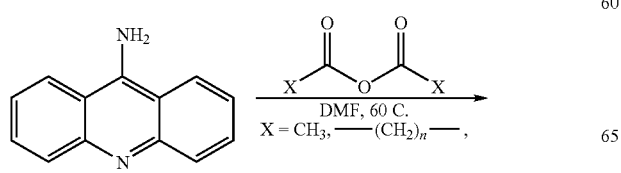

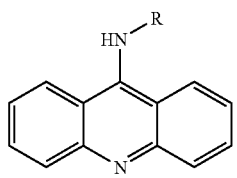

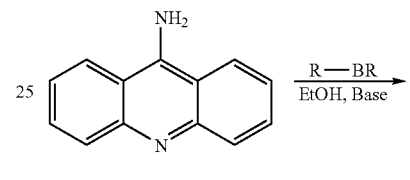

Method 4

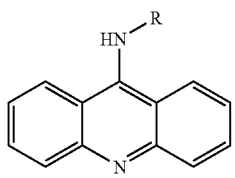

Method 5

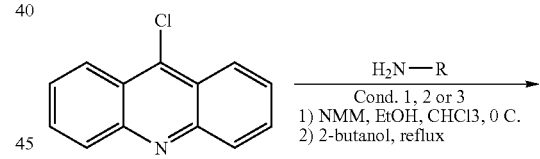

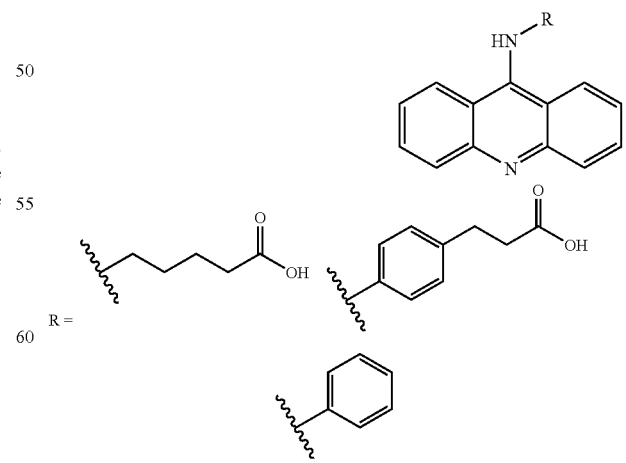

Method 6

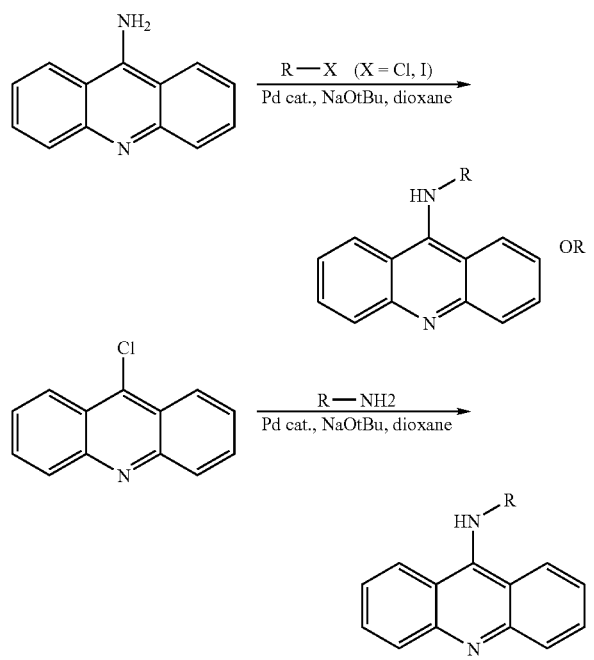

Method 7

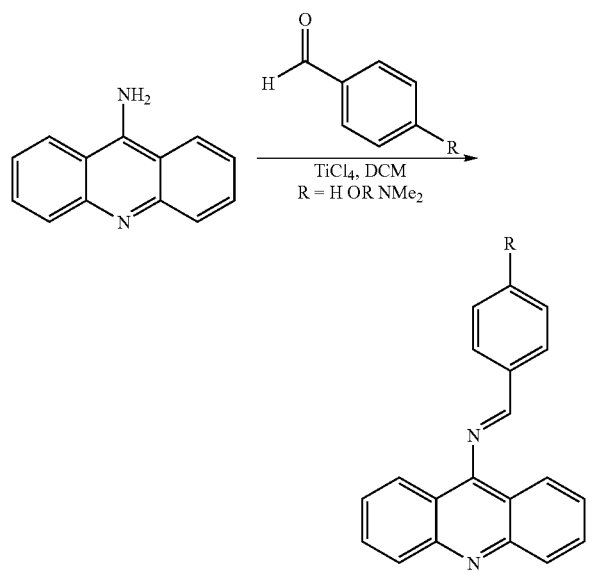

Derivatives of pyridyl nitrogen:
Method 8

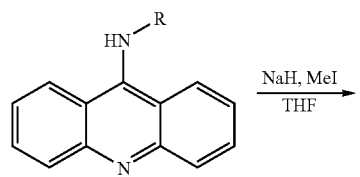

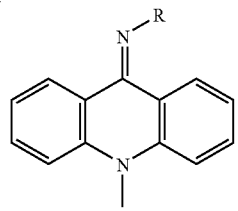

Method 9

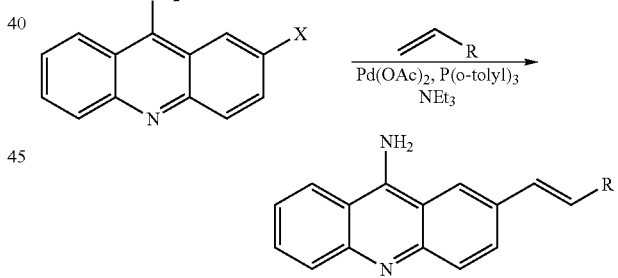

Method 10

Thus, the present invention also provides methods of making novel fluorescent dyes in accordance with formula (I), II or III comprising following a method as described in methods 1-10 described above.

The above described dyes find particular application in many biochemical and/or cell-based assays. In a simple assay, a fluorescent dye in accordance with the present invention can be used to detect whether or not a binding agent or analyte is present in a sample where the binding agent/analyte is capable of specifically binding to a partner molecule and one of said binding agent/analyte or partner is labelled with a fluorescent dye according to the present invention. Such an assay can be adapted to determine an effect a putative inhibitor or enhancer agent may have on the binding between the binding agent and its partner. Typical binding agent/analyte and partner molecules include protein/protein, protein/ nucleic acid, nucleic acid/nucleic acid, protein/small molecule and nucleic acid/small molecule partners.

For cell based assays, the assays may be carried out on live cells or using cell components, such as cell wall fragments. Any cell may be utilised including prokaryotic and eukaryotic, especially mammalian and human cells.

The assay of the present invention may typically be performed in the wells of a multiwell plate, e.g. a microtitre plate having 24, 96, 384 or higher densities of wells e.g. 864 or 1536 wells. Alternatively, the assay may be conducted in assay tubes or in the microchannels of a multifluidic device.

Conventional detection methods can be employed to measure fluorescence intensity and/or the lifetime of the label. These methods include instruments using photo-multiplier tubes as detection devices. Several approaches are possible using these methods; e.g.

i) methods based upon time correlated single photon counting (cf. Principles of Fluorescence Spectroscopy, (Chapter 4) ed. J R Lakowicz, Second Edition, 1999, Kluwer/Academic Press);

ii) methods based upon frequency domain/phase modulation (cf. Principles of Fluorescence Spectroscopy, (Chapter 5) ed. J R Lakowicz, Second Edition, 1999, Kluwer/Academic Press); and iii) methods based upon time gating (cf. Sanders et al., (1995) Analytical Biochemistry, 227 (2), 302-308).

A suitable device is the Edinburgh Instruments FLS920 fluorimeter, Edinburgh Instruments, UK.

Measurement of fluorescent intensity may be performed by means of a charge coupled device (CCD) imager, such as a scanning imager or an area imager, to image all of the wells of a multiwell plate. The LEADseeker™ system features a CCD camera allowing imaging of high density microtitre plates in a single pass. Imaging is quantitative and rapid, and instrumentation suitable for imaging applications can now simultaneously image the whole of a multiwell plate.

Details of the types of assay which may be conducted are disclosed for example in WO02/099424 and WO03/089665.

Particularly preferred biological molecules for labelling with the fluorescent dyes of the present invention are peptides or proteins. The skilled addressee is aware of methods which allow labelling at a specific site in a synthesised peptide (see e.g. Bioconjugate Techniques, G. T. Hermanson, Academic Press (1996)).

Additionally, methods for fluorescently labelling and quenching peptides have been disclosed. Thus WO 02/081509, for example, describes the use of tryptophan, tyrosine or histidine residues to internally quench fluorescence intensity within fluorescently labelled peptides. The peptides can be used to detect endo- and exo-peptidase activity. Additional and very appropriate methods relating to fluorescent lifetime measurements are described in WO 03/089663, to which the skilled reader is directed and the techniques described therein can be applied to the dyes disclosed herein.

As described therein the peptide substrate can be easily distinguished from the cleaved products on the basis of differences in, for example, the lifetime of the label. Changes in the intensity and the lifetime can be monitored if necessary, thus giving a dual parameter fit to this assay.

Thus, the present invention also relates to methods of detecting a change in fluorescence intensity and/or lifetime based on the incorporation or removal of a fluorescence modulating moiety. Typically, such a moiety may be initially present in the fluorescent molecule and binding of a partner molecule, or removal of the modulator moiety, for example, by a cleavage reaction, may lead to a modulation in fluorescence intensity and/or lifetime, which can easily be detected.

Modulators of fluorescence are moieties that typically increase or decrease the fluorescence intensity or fluorescence lifetime of a fluorophore. The mechanism of such fluorescence modulation could be but is not limited to energy transfer, electron transfer or molecular interactions. Such moieties can themselves be fluorophores or fluorescence quenches such as dabcyl or QSY35; aromatic ring systems such as naphthyl, anthracenyl, phenanthrenyl, pyrenes and derivatives thereof; tryptophan, tyrosine, phenylalanine, indolyl and derivatives thereof.

The present invention will now be further described by way of example and with reference to the Figures which show:

Figure 5:
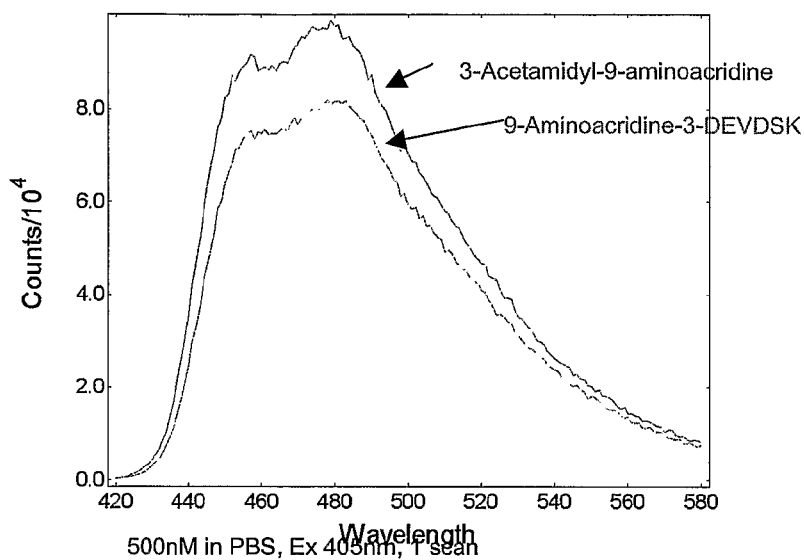
Figure 6A:
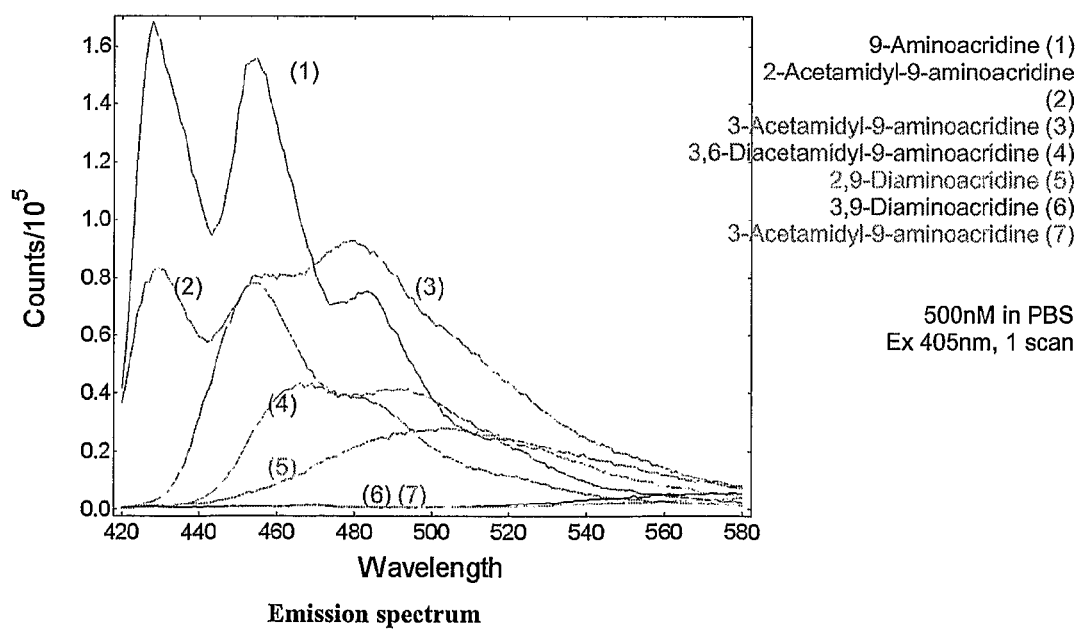
Figure 6B:
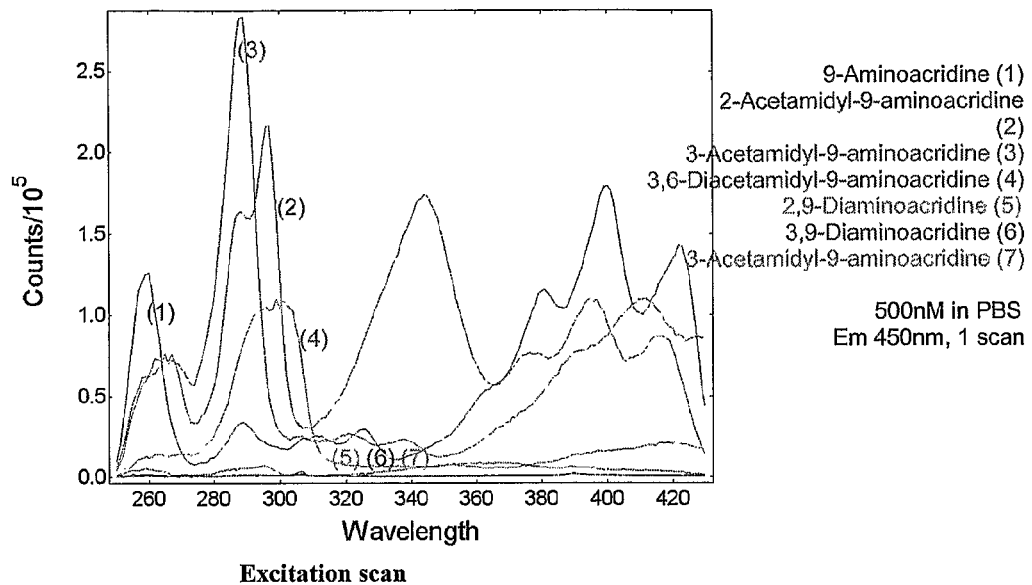
Figure 7:
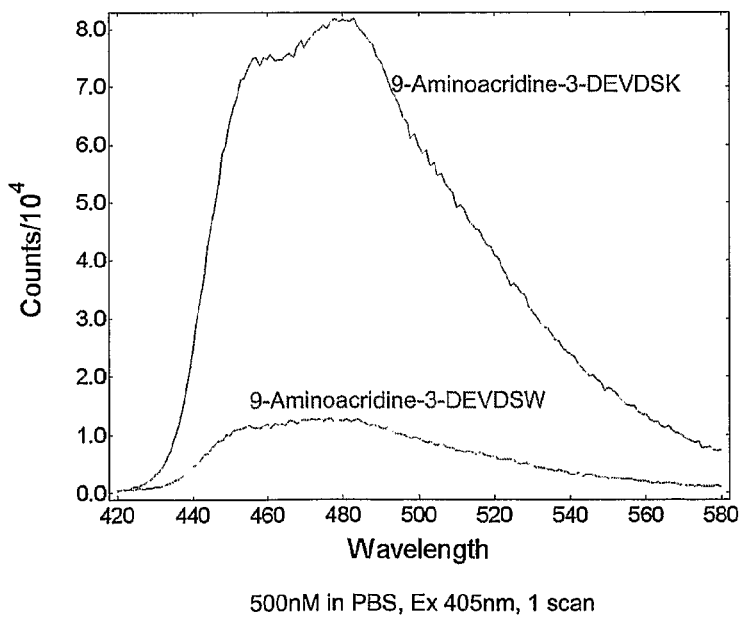

FIG. 5 shows fluorescence emission spectra of 3-acetamidyl-9-aminoacridine and the corresponding labelled peptide 9-aminoacridine-3-DEVDSK FIG. 6a fluorescence emission spectra of a series of 9-aminoacridine derivatives, derivatised at combinations of the 2, 3 and 6 positions with amino and/or acetamidyl functionalities FIG. 6b the excitation spectra of a series of 9-aminoacridine derivatives, derivatised at combinations of the 2, 3 and 6 positions with amino and/or acetamidyl functionalities FIG. 7 fluorescence emission of spectra of peptides DEVDSK and DEVDSW labelled specifically at their N-termini with 9-aminoacridine via an amide linkage at the 3-position of the fluorophore (as outlined in scheme 1)

Figure 8:
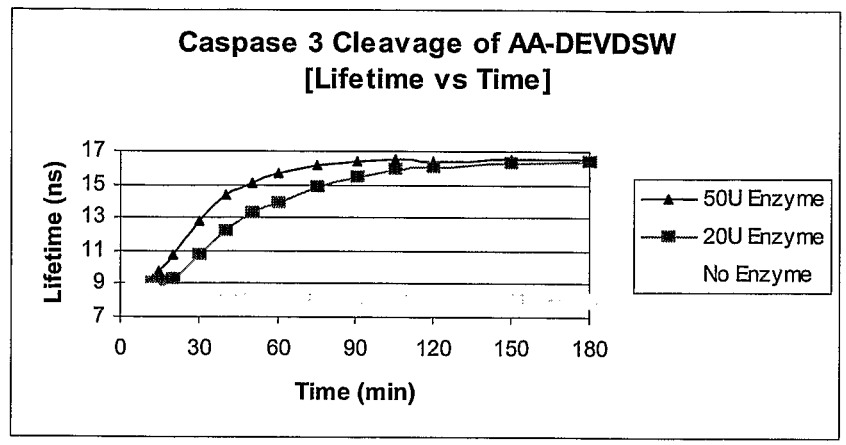

FIG. 8 Cleavage of 9-aminoacridine-3-DEVDSW (labelled specifically at its N-termini via an amide linkage at the 3-position) by caspase-3 monitored in real time through fluorescence lifetime changes.

Figure 9:
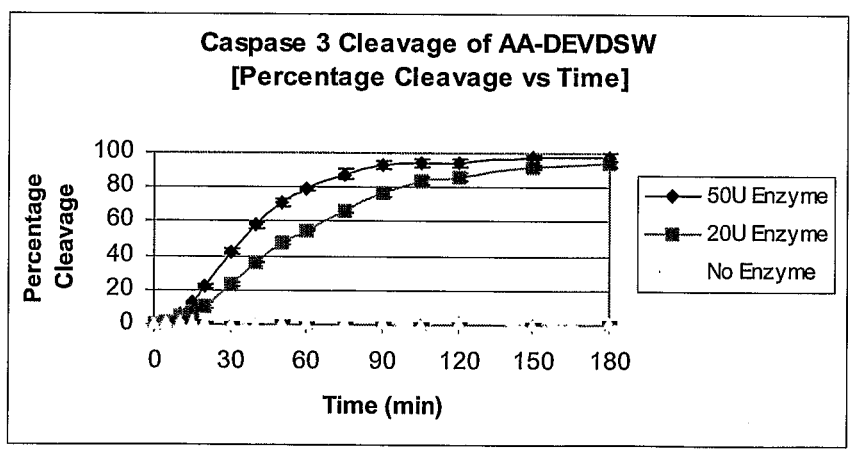
Figure 10:
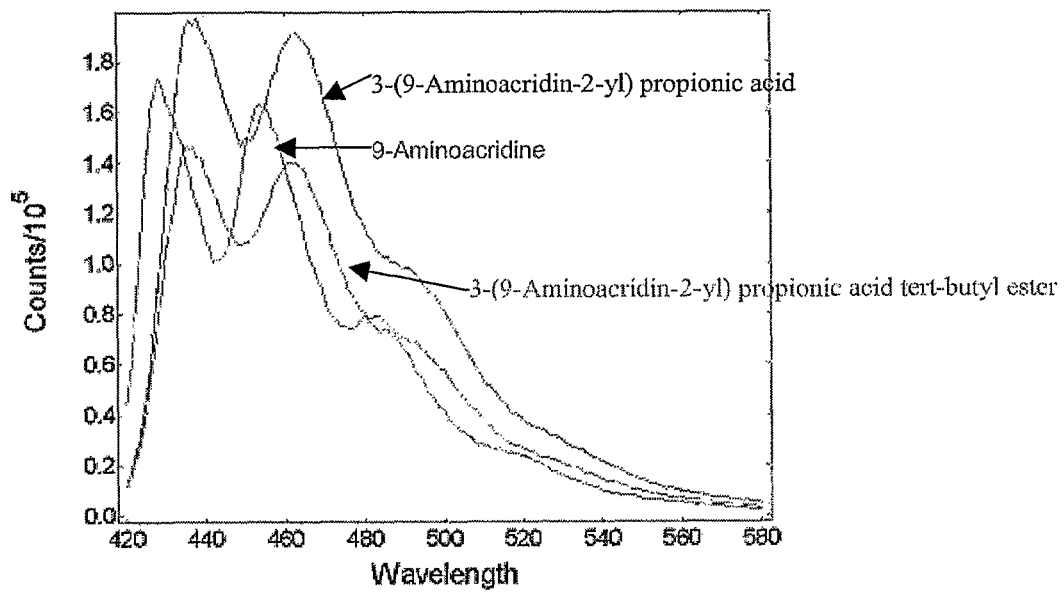

FIG. 9 Percentage cleavage of 9-aminoacridine-3-DEVDSW (labelled specifically at its N-termini via an amide linkage at the 3-position) by caspase-3 monitored in real time through fluorescence lifetime changes FIG. 10 Fluorescence emission spectra of 9-aminoacridine, 3-(9-aminoacridin-2-yl) propionic acid and 3-(9-aminoacridin-2-yl) propionic acid tertiary butyl ester.

Figure 11:
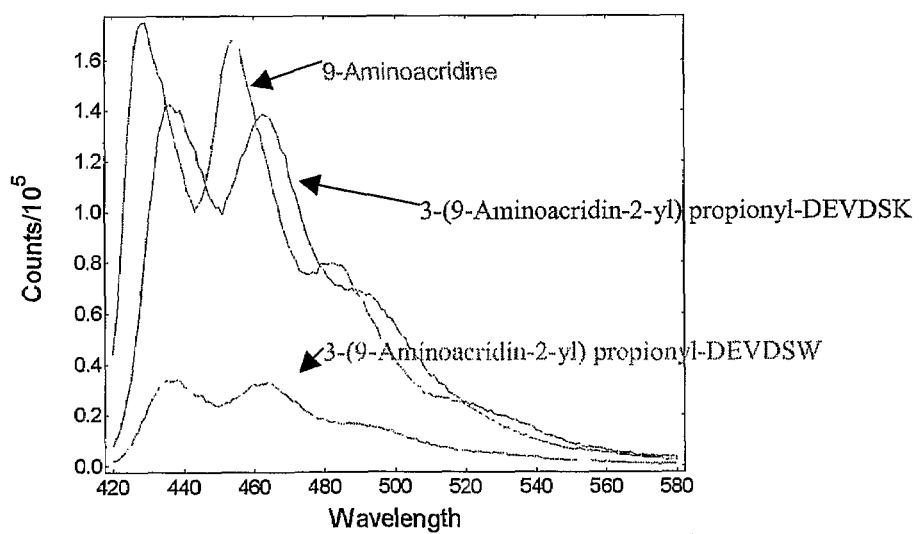

FIG. 11 Fluorescence emission spectra of 9-aminoacridine, 3-(9-aminoacridin-2-yl)-propionyl-DEVDSK and 3-(9-aminoacridin-2-yl)-propionyl-DEVDSW.

Figure 12:
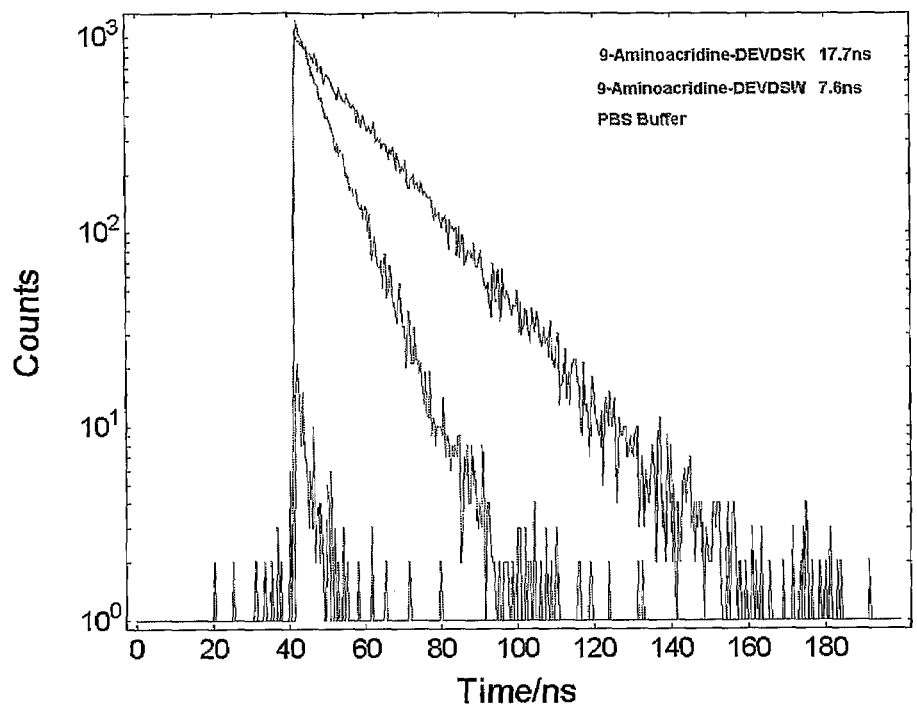

FIG. 12 Fluorescence lifetime spectra for 3-(9-aminoacridin-2-yl)-propionyl-DEVDSK and 3-(9-aminoacridin-2-yl)-propionyl-DEVDSW.

Figure 13:
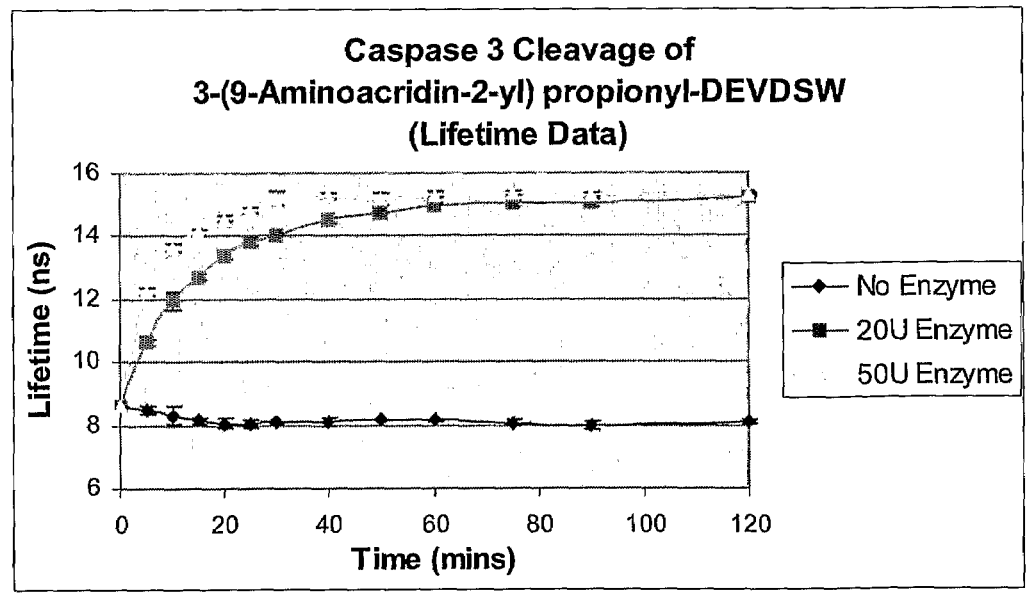

FIG. 13 Cleavage of 3-(9-aminoacridin-2-yl)-propionyl-DEVDSW by caspase-3 monitored in real time through changes in the fluorescence lifetime of the fluorophore.

Figure 14:
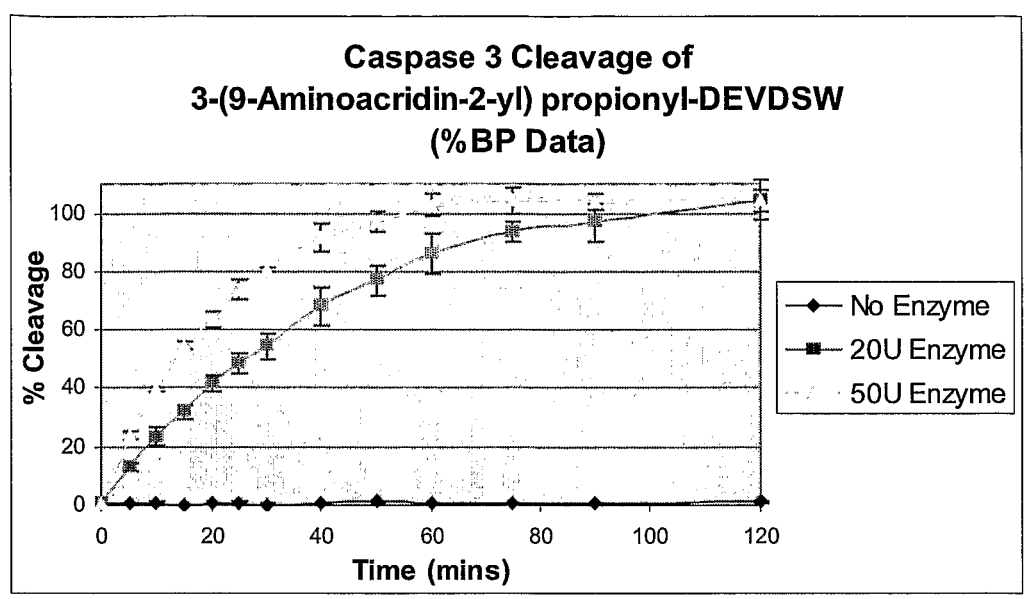

FIG. 14 Percentage cleavage of 3-(9-aminoacridin-2-yl)-propionyl-DEVDSW by caspase-3 monitored in real time.

EXAMPLES SECTION

Example 1

Synthesis of Thioacridone

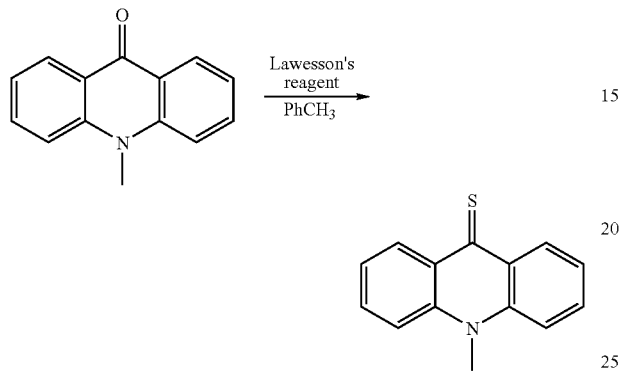

Procedure

A mixture of N-methyl acridone (250 m, 1.2 mmol) and Lawesson's reagent (540 mg, 1.34 mmol) in toluene (15 ml) was stirred under a nitrogen atmosphere for 10 minutes and then heated at reflux for 8 hours. On cooling to room temperature, the toluene was removed in vacuo and the thioacridone was recrystallised from DCM to give a dark orange solid.

$^1$H NMR, IR and mass spec data were all in agreement with the literature (J. Pharm. Sci. 1971, 60, 1239).

Figure 1:
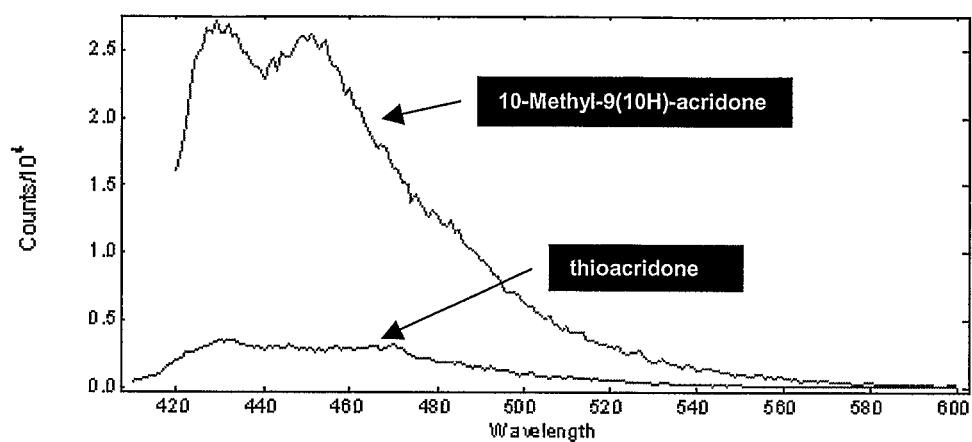
FIG. 1 shows fluorescence emission spectra of 10-methyl-9(10H)-thioacridone and 10-methyl-9(10H)-acridone.

Fluorescence emission spectra of 10-methyl-9(10H)-thioacridone (N-methyl thioacridone) and 10-methyl-9(10H)-acridone (N-methylacridone) in 140 mM NaCl, 10 mM phosphate buffer pH 7.4 upon excitation at 405 nm, were obtained. The thioacridone concentration is 500 nM and the 10-methyl-9(10H)-acridone (N-methylacridone) concentration is 100 nM. Results are shown in FIG. 1.

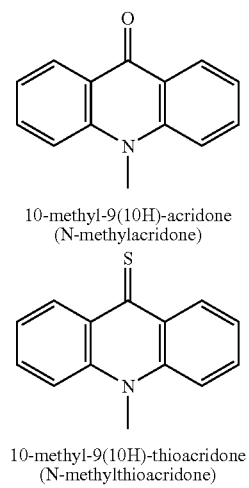

10-methyl-9(10H)-acridone
(N-methylacridone)

10-methyl-9(10H)-thioacridone
(N-methylthioacridone)

In an attempt to generate acridone derivatives with enhanced fluorescence properties N-methyl thioacridone was generated and its fluorescence properties compared to N-methyl acridone. However, as can be seen from the fluorescence emission spectra, substitution of the carbonyl oxygen of acridone with sulphur, considerably attenuates the fluorescence of the molecule. The fluorescence emission intensity of the thioacridone is considerably less fluorescent than the corresponding methyl-acridone derivative.

Example 2

Figure 2:
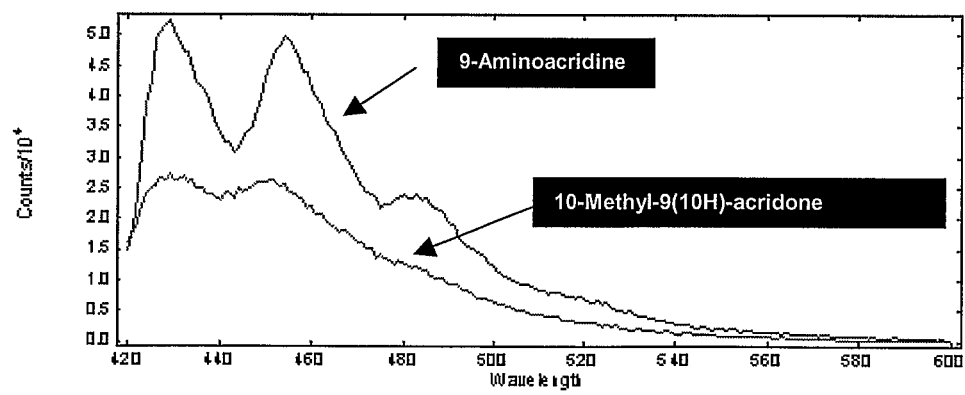
FIG. 2 shows fluorescence emission spectra of 9-aminoacridine and 10-methyl-9(10H)-acridone.

Fluorescence emission spectra of 9-aminoacridine and 10-methyl-9(10H)-acridone (N-methylacridone) upon excitation at 405 nm. Both compounds at a concentration of 100 nM in 140 mM NaCl, 10 mM phosphate buffer pH 7.4, were obtained. Results are shown in FIG. 2.

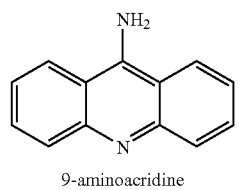 [SMILES: Nc1c2ccccc2nc2ccccc12]

9-aminoacridine

Comparison of the fluorescence emission spectra of 9-aminoacridine and N-methyl acridone, at the same concentration, clearly shows that the 9-aminoacridine is considerably brighter than N-methylacridone. In general brighter dyes are more advantageous for fluorescence based applications. Consequently acridine derivatives with amino containing substitutents at the 9-position are considerably enabling as fluorescence reporters.

Example 3

Figure 3:
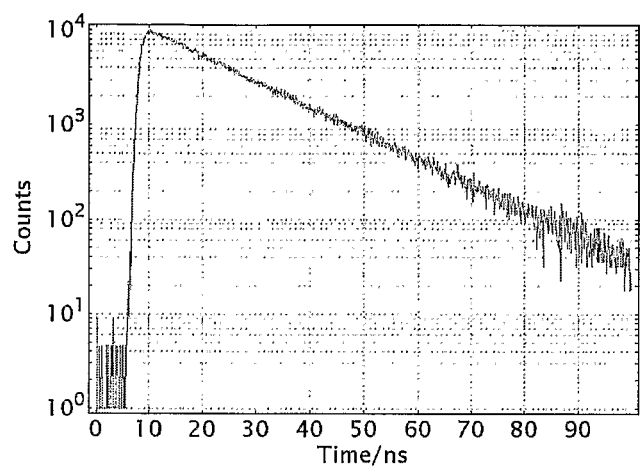
FIG. 3 shows representative fluorescence lifetime measurement for 9-aminoacridine.

Fluorescence Lifetime Measurements of N-methyl acridone, N-methyl thioacridone and 9-aminoacridine Fluorescence lifetimes were determined by time-correlated single photon counting using an Edinburgh Instruments FLS920 fluorimeter. Samples were excited at 405 nm with detection at 450 nm. Measurements were recorded in 10 mM phosphate buffered saline pH 7.4. The fluorescence lifetime emission spectrum of 9-aminoacridine is shown in FIG. 3.

TABLE 1

| Compound | Structure | Fluorescence Lifetime (nsecs) in PBS pH 7.4 |
| --- | --- | --- |
| N-methyl acridone | 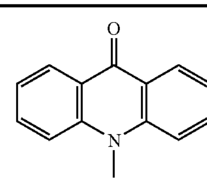 | 13.9 |
| N-methyl thioacridone | 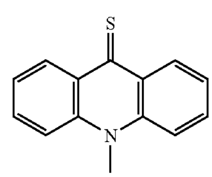 [SMILES: Cn1c2ccccc2c(=S)c2ccccc21] | Not applicable |

TABLE 1-continued

| Compound | Structure | Fluorescence Lifetime (nsecs) in PBS pH 7.4 |
|---|---|---|
| 9-aminoacridine | 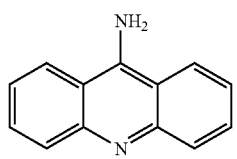 [SMILES: Nc1c2ccccc2nc2ccccc12] | 16.0 |

| NMR | $^1$H | $^{13}$C |
|---|---|---|
| IR | 3094, 1751, 1664, 1587, 1205, 756 cm$^{-1}$ | |
| UV | 405 nm, 425 nm | |
| MS | 281.1, 336.1 | |
| TLC | 0.15 (DCM/MeOH) | |

Example 4

Derivatisation of 9-aminoacridine at the 9-amino position

Figure 4:
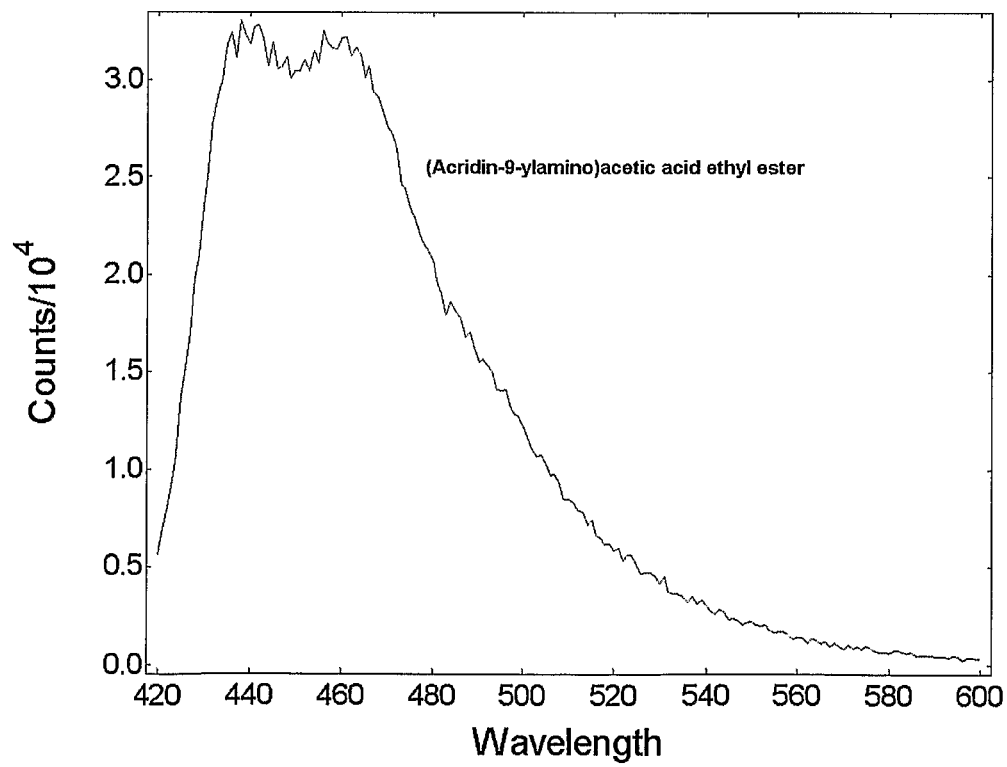
FIG. 4 shows fluorescence emission spectra of (Acridin-9-ylamino)acetic acid ethyl ester.

Fluorescence emission spectrum of (Acridin-9-ylamino) acetic acid ethyl ester at 100 nM concentration in 140 mM NaCl, 10 mM phosphate buffer pH 7.4 upon excitation at 405 nm is shown in FIG. 4.

Fluorescence Lifetime Measurement

The fluorescence lifetime was shown to be 14.9 ns. Excitation wavelength 405 nm and emission wavelength 450 nm.

Experimental Procedure

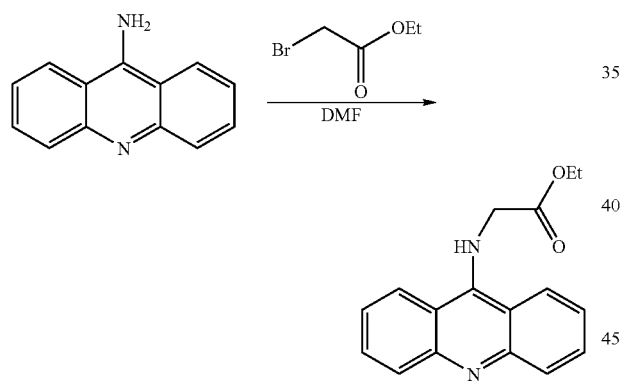

100 mg of 9-Aminoacridine (from 9-Aminoacridine.H$_2$O.HCl (Aldrich) dissolved into saturated NaHCO$_{3(aq)}$ and extracted to DCM, drying with Na$_2$CO$_3$) was dissolved in 2 ml of DMF. Bromoethyl acetate (86.5 µL) was injected and the mixture was heated at 80-85° C. After 1 hour, the reaction starts to darken from bright yellow to brownish. Reaction was continued for another 4 hours. The DMF was removed under vacuum via azeotrope with toluene (3×15 ml) and toluene removed via azeotrope with DCM. Overnight drying without any change TLC in DCM/MeOH 9:1 shows at least eight compounds all fluorescent under UV lamp. MS shows four main components (M/Z=195 (M+1,9-aminoacridine); 281 (M+1, monoalkylated); 336 (unknown) and 367 (M+1 dialkylated). Chromatographic purification in silica with DCM to DCM/MeOH 96:4 gives the monoalkylated aminoacridine (281) with the M/Z=336 impurity present in all its fractions. On evaporation 36 mg were isolated as a yellow-orange solid.

Example 5

Synthesis of Acetamidyl-9-aminoacridine Derivatives (1) 9-Aminoacridine

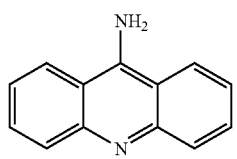 [SMILES: Nc1c2ccccc2nc2ccccc12]

Aminoacridine hydrochloride (2 g, 8.7 mmol) was added to a mixture of sodium hydroxide (0.7 g, 17.4 mmol) in water (100 mL) and EtOAc (100 mL) stirred for 15 min. The EtOAc layer was separated and the aqueous layer was washed with EtOAc (3×50 mL). The organic fractions were combined and dried (Na$_2$CO$_3$), filtered and concentrated in vacuo to give an orange crystalline solid (1.7 g, quantitative).

(2) 2-Acetamidyl-9-aminoacridine

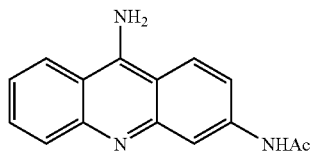 [SMILES: CC(=O)Nc1ccc2c(N)c3ccccc3nc2c1]

To a 5 mL rbf equipped with condenser and a nitrogen bubbler were charged 2,9-diaminoacridine (100 mg, 0.48 mmol) and acetic acid (300 µL). To the resulting solution was added acetic anhydride (47 µL, 0.50 mmol). The reaction mixture was heated to reflux for 10 min under a nitrogen atmosphere. LCMS showed only formation of expected product and some traces of starting material. The reaction mixture was concentrated to dryness. NMR showed desired product, alkanes impurities coming from starting material sample and acetic acid left. The residue was dissolved in water and washed with DCM to remove the alkanes impurities. The aqueous layer was lyophilised to afford 2-acetamidyl-9-ami-

(3) 3-Acetamidyl-9-aminoacridine

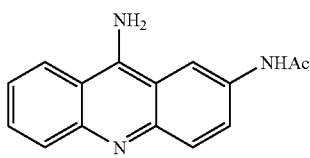 [SMILES: CC(=O)Nc1ccc2nc3ccccc3c(N)c2c1]

To a 25 mL rbf equipped with a nitrogen bubbler were charged 3,9-diaminoacridine (50 mg, 0.24 mmol) and anhydrous DCM (2 mL). To the resulting red suspension was added acetic anhydride (25 µL, 0.26 mmol) followed by triethylamine (37 µL, 0.26 mmol). The reaction mixture was stirred overnight at room temperature under a nitrogen atmosphere. LCMS showed incomplete reaction but only formation of expected product. Starting material was not really soluble in DCM. Pyridine (0.5 mL) was thus added and the mixture stirred overnight. LCMS still showed incomplete reaction. A further portion of acetic anhydride (25 µL, 0.26 nmol) was added and the reaction mixture was stirred at room temperature over three days. LCMS showed reaction completion.

The reaction mixture was concentrated to dryness. The residue was partitioned between EtOAc and water, and then the layers were separated. The aqueous layer was extracted with more EtOAc (twice) and concentrated in vacuo to afford a dark orange solid. This solid was slurried in diethyl ether and filtered to yield pure 3-acetamidyl-9-aminoacridine as a yellow solid (35 mg, 58%). Analyses by $^1$H NMR and LCMS conformed to structure.

(4) 3,6-Diacetamidyl-9-aminoacridine

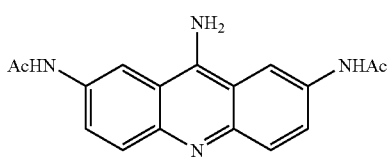 [SMILES: CC(=O)Nc1ccc2nc3ccc(NC(C)=O)cc3c(N)c2c1]

3-Acetamidyl-6,9-diaminoacridine (10 mg, 0.048 mmol) was dissolved in acetic acid (5 mL) and heated at reflux under a nitrogen atmosphere. Acetic anhydride (4.7 µL, 0.05 mmol) was added and reflux was continued for 10 min. On cooling to room temperature, the solution was concentrated to dryness and the residue was dissolved in water (10 mL) and washed with DCM (3×10 mL). The aqueous layer was lyophilised to give a brown solid.

(5) 2,9-Diaminoacridine

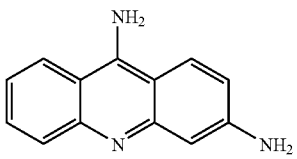

Step 1: Synthesis of 5-nitrodiphenylamine-2-carboxylic acid by Ullmann reaction.

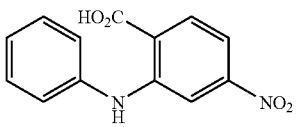 [SMILES: O=C(O)c1ccc([N+](=O)[O-])cc1Nc1ccccc1]

Aniline (2.9 mL, 31.75 mmol) and 2-chloro-4-nitrobenzoic acid (1 g, 4.96&mol) were charged to a 50 mL rbf equipped with a reflux condenser and nitrogen bubbler. To the resulting mixture was added copper (II) acetate (45 mg) followed by anhydrous potassium carbonate (789 mg, 5.71 mmol). The reaction mixture was heated to 185° C. for 2 hours, and then cooled to room temperature. The brown solid was diluted with water and acidified with an aqueous hydrochloric acid 2M solution until pH of 2 was reached. The mixture was triturated and the suspension was allowed to stir until a green powder appeared. The solid was filtered, washed with an excess of water to remove aniline and allowed to suck dry over 1 hour. The product was obtained as a green powdery solid (1.24 g). Purification by dry chromatography using a gradient elution (DCM→DCM:MeOH 99:1) afforded pure 5-nitrodiphenylamine-2-carboxylic acid as a yellow-orange powdery solid (672 mg, 52%). Analyses by $^1$H NMR and LCMS conformed to structure.

Step 2: Cyclisation of 5-nitrodiphenylamine-2-carboxylic acid using POCl$_3$.

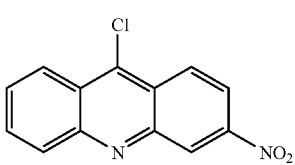

5-Nitrodiphenylamine-2-carboxylic acid (500 mg, 1.94 mmol) and phosphorus oxychloride (4 mL) were charged to a 25 mL rbf equipped with a reflux condenser and nitrogen bubbler. The reaction mixture was refluxed at 140° C. for 30 min then cooled to 0° C. The excess POCl$_3$ was washed out with petroleum ether. The sticky residue was carefully quenched with ice and basified with an aqueous ammonia 28% solution (the flask was kept cold with an ice bath). The resulting mixture was triturated until the product was converted into a yellow powder, which was extracted with chloroform. The combined organic layers were dried over magnesium sulphate, filtered and concentrated in vacuo to yield the crude product (489 mg). Purification by flashmaster column eluting with DCM afforded pure 2-nitro-9-chloroacridine as a yellow solid (423 mg, 85%). Analyses by ¹H NMR and LCMS conformed to structure.

Step 3: Synthesis of 2-nitro-9-aminoacridine by amination.

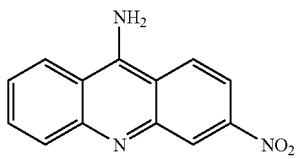

To a 50 mL rbf equipped with a reflux condenser and nitrogen bubbler were charged 2-nitro-9-chloroacridine (422 mg, 1.63 mmol) and phenol (1.58 g, 16.80 mmol). The mixture was heated to 70° C. Stirring was continued and powdered ammonium carbonate (211 mg) was added as rapidly as the vigorous effervescence permitted. The temperature was quickly raised to 120° C. and the reaction mixture was stirred at this temperature for a further 1 hour. After cooling to 30° C., acetone (4 mL) was added and the flask was cooled to 0° C. for 1 hour to precipitate 9-aminoacridine hydrochloride. The suspension was filtered and washed free from phenol with acetone (1.8 mL). The product HCl salt was obtained as an orange solid (449 mg). The solid was slurried in water (28 mL) and 1 g of sodium hydroxide solid was added. The mixture was stirred at room temperature for 1 hour, filtered and washed with water. 2-Nitro-9-aminoacridine was obtained as a dark red solid (352 mg, 90%). ¹H NMR and LCMS analyses conformed to structure.

Step 4: Reduction of the nitro functionality to yield 2,9-diaminoacridine.

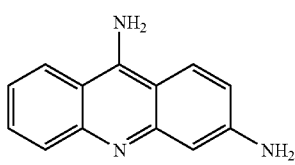 [SMILES: O=[N+]([O-])c1ccc2c(Cl)c3ccccc3nc2c1]

To a 50 mL rbf equipped with a nitrogen bubbler were charged 2-nitro-9-aminoacridine (350 mg, 1.46 mmol) and ethyl acetate (7.4 mL). Methanol (3.7 mL) and Pd/Alumina 10% (47 mg) were added and the reaction mixture was stirred to a fine suspension. Ammonium formate (185 mg, 2.93 mmol) was added and the mixture was stirred for 20 min at room temperature. A further portion of ammonium formate (277 mg, 4.39 nmol) was then added. Stirring was maintained overnight. LCMS analysis indicated reaction completion.

The suspension was filtered and washed with ethyl acetate to afford the crude product as a yellow solid (257 mg). The solid was dissolved in water and the solution was neutralised by addition of an aqueous hydrochloric acid 2M solution. Filtration removed catalyst and some basic impurities. The filtrate was poured into an excess of an aqueous sodium hydroxide 2.5M solution to precipitate the desired product. The solid was collected by filtration, dissolved in THF and filtered. The filtrate was concentrated in vacuo and the residue slurried in hexane. Filtration afforded 2,9-diaminoacridine as an orange solid (115 mg, 38%). ¹H NMR and LCMS analyses conformed to structure.

(6) 3,9-Diaminoacridine

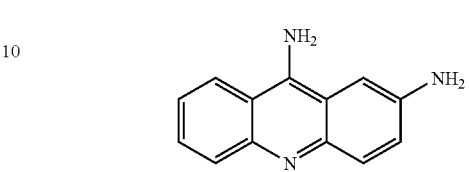

Step 1: Synthesis of 4-nitrodiphenylamine-2-carboxylic acid by Ullmann reaction.

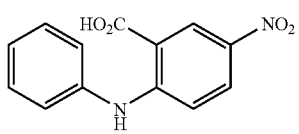 [SMILES: O=C(O)c1cc([N+](=O)[O-])ccc1Nc1ccccc1]

Aniline (29 mL, 317.5 mmol) and 2-chloro-5-nitrobenzoic acid (10 g, 49.61 mmol) were charged to a 250 mL rbf equipped with a reflux condenser and nitrogen bubbler. To the resulting mixture was added copper (II) acetate (450 mg) followed by anhydrous potassium carbonate (7.9 g, 57.05 mmol). The reaction mixture was heated to 185° C. for 2 hours, and then cooled to room temperature. The dark green solid was diluted with water and acidified with an aqueous hydrochloric acid solution until pH of 2 was reached. The mixture was triturated and the suspension was allowed to stir until a green powder appeared. The solid was filtered, washed with an excess of water to remove aniline and allowed to suck dry over 1 hour. 4-Nitrodiphenylamine-2-carboxylic acid was obtained as a green powdery solid (12.0 g, 93%). Analyses by ¹H NMR and LCMS conformed to structure.

Step 2: Cyclisation of 4-nitrodiphenylamine-2-carboxylic acid using POCl₃.

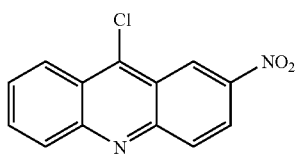 [SMILES: O=[N+]([O-])c1ccc2nc3ccccc3c(Cl)c2c1]

4-Nitrodiphenylamine-2-carboxylic acid (8 g, 30.98 mmol) and phosphorus oxychloride (80 mL) were charged to a 250 mL rbf equipped with a reflux condenser and nitrogen bubbler. The reaction mixture was refluxed at 140° C. for 5 hours. The excess POCl₃ was removed in vacuo. The reaction mixture was carefully quenched with ice, basified with an aqueous ammonia solution (the flask was kept cold with an ice bath), and extracted with DCM (2×500 ml). The combined organic layers were dried over magnesium sulphate, filtered and concentrated to yield the crude product. Purification by dry chromatography using a gradient elution (Hexane→Hexane:EtOAc 80:20) afforded pure 3-nitro-9-chloroacridine as a yellow solid (3.8 g, 47%). Analyses by ¹H NMR and LCMS conformed to structure.

Step 3: Synthesis of 3-nitro-9-aminoacridine by amination.

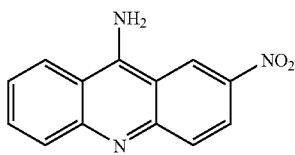 [SMILES: Nc1c2ccccc2nc2ccc([N+](=O)[O-])cc12]

To a 50 mL rbf equipped with a reflux condenser and nitrogen bubbler were charged 3-nitro-9-chloroacridine (1.49 g, 5.75 mmol) and phenol (5.57 g, 59.24 mmol). The mixture was heated to 70° C. Stirring was continued and powdered ammonium carbonate (743 mg, 7.73 mmol) was added as rapidly as the vigorous effervescence permitted. The temperature was quickly raised to 120° C. and the reaction mixture was stirred at this temperature for a further 1 hour. After cooling to 30° C., acetone (14 mL) was added and the flask was cooled to 0° C. for 1 hour to precipitate 9-aminoacridine hydrochloride. The suspension was filtered and washed free from phenol with acetone (6 mL). The product HCl salt was obtained as an orange solid (1.78 g). The solid was slurried in water (100 mL) and 3.7 g of sodium hydroxide solid was added. The mixture was stirred at room temperature for 2 hours, filtered and washed with water. 3-Nitro-9-aminoacridine was obtained as a red solid (1.29 g, 94%). $^1$H NMR and LCMS analyses conformed to structure.

Step 4: Reduction of the nitro functionality to yield 3,9-diaminoacridine.

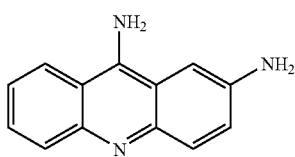 [SMILES: Nc1ccc2nc3ccccc3c(N)c2c1]

To a 250 mL rbf equipped with a nitrogen bubbler were charged 3-nitro-9-aminoacridine (1.29 g, 5.39 mmol) and ethyl acetate (27.2 mL). Methanol (13.6 mL) and Pd/Alumina 10% (174 mg) were added and the reaction mixture was stirred to a fine suspension. Ammonium formate (680 mg, 10.78 mmol) was added and the mixture was stirred for 20 min at room temperature. A further portion of ammonium formate (1.02 g, 16.18 mmol) was then added. Stirring was maintained for 1 hour. TLC and LCMS analysis indicated reaction completion.

The suspension was filtered and washed with ethyl acetate to afford the crude product as an orange solid (1.99 g). The solid was dissolved in water and the solution was neutralised by addition of an aqueous hydrochloric acid 2M solution. Filtration removed catalyst and some basic impurities. The filtrate was poured into an excess of an aqueous sodium hydroxide 2.5M solution to precipitate the desired product. The solid was collected by filtration, dissolved in THF and filtered. The filtrate was concentrated in vacuo to afford 3,9-diaminoacridine as a brown solid (915 mg, 81%). $^1$H NMR and LCMS analyses conformed to structure.

(7) 3-Acetamidyl-6,9-diaminoacridine

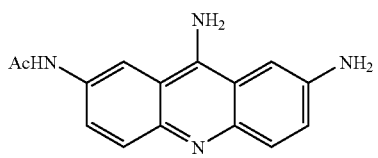 [SMILES: CC(=O)Nc1ccc2nc3ccc(N)cc3c(N)c2c1]

Step 1: Synthesis of 4'-acetamidyl-4-nitrodiphenylamine-2-carboxylic acid by Ullmann reaction.

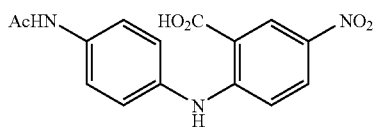 [SMILES: CC(=O)Nc1ccc(Nc2ccc([N+](=O)[O-])cc2C(=O)O)cc1]

4'-Aminoacetanilide (7.45 g, 49.61 mmol) and 2-chloro-5-nitrobenzoic acid (10 g, 49.61 mmol) were charged to a 250 mL rbf equipped with a reflux condenser and nitrogen bubbler. To the resulting mixture was added copper (II) acetate (450 mg) followed by anhydrous potassium carbonate (7.9 g, 57.05 mmol). These solids were well stirred to ensure uniform mixture, and then heated to 170° C. as a melt for 2 hours. After cooling to room temperature, the black solid was diluted with water and acidified with an aqueous hydrochloric acid 2M solution until pH of 2 was reached. The mixture was triturated until a black powder appeared. The solid was filtered, washed with an excess of water and allowed to suck dry over 1 hour. The product was obtained as a dark brown powdery solid (11.89 g). Purification by dry chromatography using a gradient elution (DCM→DCM:MeOH 90:10) afforded 4'-acetamidyl-4-nitrodiphenylamine-2-carboxylic acid as a red solid (4.73 g, 30%). Analyses by $^1$H NMR and LCMS conformed to structure and confirmed purity >90%. Product used in the next step without further purification.

Step 2: Cyclisation of 4'-acetamidyl-4-nitrodiphenylamine-2-carboxylic acid using POCl$_3$.

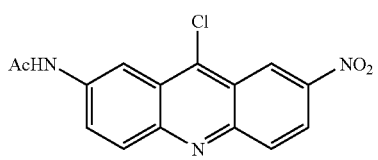 [SMILES: CC(=O)Nc1ccc2nc3ccc([N+](=O)[O-])cc3c(Cl)c2c1]

4'-Acetamidyl-4-nitrodiphenylamine-2-carboxylic acid (500 mg, 1.59 mmol) and phosphorus oxychloride (4 mL) were charged to a 25 mL rbf equipped with a reflux condenser and nitrogen bubbler. The reaction mixture was refluxed at 140° C. for 20 min then cooled to 0° C. The excess POCl$_3$ was washed out with petroleum ether. The sticky residue was carefully quenched with ice and basified with an aqueous ammonia 28% solution (the flask was kept cold with an ice bath). The resulting mixture was triturated until the product was converted into a black powder, which was extracted with chloroform. The combined organic layers were dried over magnesium sulphate, filtered and concentrated in vacuo to yield the crude product (400 mg). Purification by flashmaster column eluting with DCM→DCM:EtOAc 60:40 afforded pure 3-acetamidyl-6-nitro-9-chloroacridine as an orange solid (126 mg, 25%). Analyses by $^1$H NMR and LCMS conformed to structure.

Step 3: Synthesis of 3-acetamidyl-6-nitro-9-aminoacridine by amination.

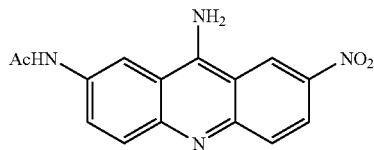 [SMILES: CC(=O)Nc1ccc2nc3ccc([N+](=O)[O-])cc3c(N)c2c1]

To a 50 mL rbf equipped with a reflux condenser and nitrogen bubbler were charged 3-acetamidyl-6-nitro-9-chloroacridine (208 mg, 0.66 mmol) and phenol (639 mg, 6.79 mmol). The mixture was heated to 70° C. Stirring was continued and powdered ammonium carbonate (93 mg) was added as rapidly as the vigorous effervescence permitted. The temperature was quickly raised to 120° C. and the reaction mixture was stirred at this temperature for a further 1 hour. After cooling to 30° C. was added acetone (1.8 mL) and the flask was cooled to 0° C. for 1 hour to precipitate 9-aminoacridine hydrochloride. The suspension was filtered and washed free from phenol with acetone (1 mL). The product HCl salt was obtained as an orange solid (198.5 mg). The solid was slurried in water (12 mL) and 425 mg of sodium hydroxide solid was added. The mixture was stirred at room temperature for 1 hour, filtered and washed with water to yield 3-acetamidyl-6-nitro-9-aminoacridine as a red solid (141 mg). Attempts of purification by column and slurring in different solvent were unsuccessful. Final product (112 mg) still contained some impurities. $^1$H NMR and LCMS analyses conformed to structure and confirmed purity >90%.

Step 4: Reduction of the nitro functionality to yield 3-acetamidyl-6,9-diaminoacridine.

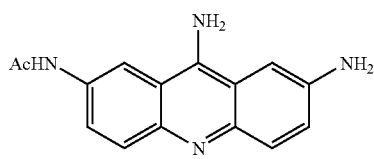 [SMILES: CC(=O)Nc1ccc2nc3ccc(N)cc3c(N)c2c1]

To a 50 mL rbf equipped with a nitrogen bubbler were charged 3-acetamidyl-6-nitro-9-aminoacridine (110 mg, 0.37 mmol) and ethyl acetate (1.9 mL). Methanol (950 µL) and Pd/Alumina 10% (12 mg) were added and the reaction mixture was stirred to a fine suspension. Ammonium formate (47 mg, 0.74 mmol) was added and the mixture was stirred for 20 min at room temperature. A further portion of ammonium formate (70 mg, 1.11 mmol) was then added. Stirring was maintained overnight. The suspension was filtered and washed with ethyl acetate to afford the crude product (106 mg). The solid was dissolved in water and washed with ethyl acetate. The aqueous layer was concentrated in vacuo to afford 3-acetamidyl-6,9-diaminoacridine as a brown solid (29 mg, 29%). $^1$H NMR and LCMS analyses conformed to structure.

(8) 1,9-Diaminoacridine

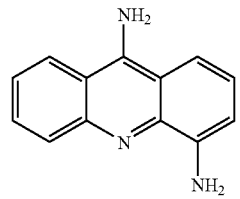 [SMILES: Nc1c2ccccc2nc2c(N)cccc12]

Step 1: Synthesis of 6-nitrodiphenylamine-2-carboxylic acid by Ullmann reaction.

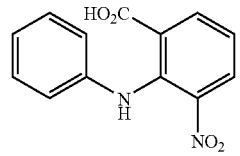 [SMILES: O=C(O)c1cccc([N+](=O)[O-])c1Nc1ccccc1]

Aniline (2.9 mL, 31.75 mmol) and 2-chloro-3-nitrobenzoic acid (1 g, 4.96 mmol) were charged to a 50 mL rbf equipped with a reflux condenser and nitrogen bubbler. To the resulting mixture was added copper (II) acetate (45 mg) followed by anhydrous potassium carbonate (789 mg, 5.71 mmol). The reaction mixture was heated to 160° C. for 1 hour, and then cooled to room temperature. The residue was diluted with water and acidified with an aqueous hydrochloric acid 2M solution until pH of 2 was reached. The mixture was triturated until a green powder appeared. The solid was filtered, washed with an excess of water to remove aniline and allowed to suck dry over 1 hour. 6-Nitrodiphenylamine-2-carboxylic acid was obtained as a green powdery solid (1.26 g, 98%). Analyses by $^1$H NMR and LCMS conformed to structure.

Step 2: Cyclisation of 6-nitrodiphenylamine-2-carboxylic acid using POCl$_3$.

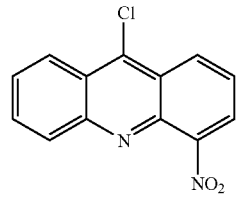 [SMILES: O=[N+]([O-])c1cccc2c(Cl)c3ccccc3nc12]

6-Nitrodiphenylamine-2-carboxylic acid (654 mg, 2.53 mmol) and phosphorus oxychloride (5 mL) were charged to a 25 mL rbf equipped with a reflux condenser and nitrogen bubbler. The reaction mixture was refluxed at 140° C. for 1 hour then cooled to 0° C. The excess POCl$_3$ was washed out with petroleum ether. The sticky residue was carefully quenched with ice and basified with an aqueous ammonia 28% solution (the flask was kept cold with an ice bath). The resulting mixture was triturated until the product was converted into powder, which was extracted with chloroform. The combined organic layers were dried over magnesium sulphate, filtered and concentrated in vacuo to yield crude 1-nitro-9-chloroacridine as a brown solid (714 mg). $^1$H NMR conformed to chloroacridine structure but also presence of 1-nitroacridone (11%). The product was used in the next step without further purification due to its instability on silica.

Step 3: Synthesis of 1-nitro-9-aminoacridine by amination.

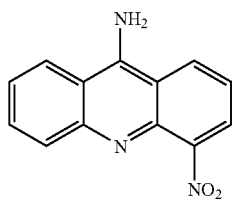

To a 50 mL rbf equipped with a reflux condenser and nitrogen bubbler were charged crude 1-nitro-9-chloroacridine (714 mg, 2.76 mmol) and phenol (2.67 g, 28.42 mmol). The mixture was heated to 70° C. Stirring was continued and powdered ammonium carbonate (360 mg) was added as rapidly as the vigorous effervescence permitted. The temperature was quickly raised to 120° C. and the reaction mixture was stirred at this temperature for a further 1 hour. After cooling to 30° C., acetone (7.2 mL) was added and the flask was cooled to 0° C. for 1 hour. The suspension was filtered and washed free from phenol with acetone (3 mL) to give an orange solid (270 mg) corresponding to a mixture of 1-nitroacridone (84%) and 1-nitro-9-aminoacridine (26%). After removal of acetone, an aqueous sodium hydroxide solution (2.14 g in 28.6 mL of water) was added to the filtrate. The precipitate was collected and triturated with an aqueous acetic acid 2% solution (21.4 mL). The black insoluble material was filtered off and washed with more solvent. The combined filtrates on basification with an aqueous sodium hydroxide solution yielded a red solid (333 mg). Purification by flashmaster column afforded pure 1-nitro-9-aminoacridine as a red solid (162 mg, 25%). $^1$H NMR and LCMS analyses conformed to structure.

Step 4: Reduction of the nitro functionality to yield 1,9-diaminoacridine.

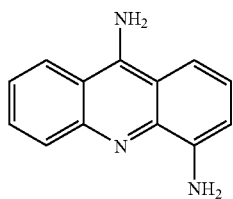 [SMILES: Nc1c2ccccc2nc2c(N)cccc12]

To a 50 mL rbf equipped with a nitrogen bubbler were charged 1-nitro-9-aminoacridine (162 mg, 0.68 mmol) and ethyl acetate (3.4 mL). Methanol (1.7 mL) and Pd/Alumina 10% (22 mg) were added and the reaction mixture was stirred to a fine suspension. Ammonium formate (85 mg, 1.35 mmol) was added and the mixture was stirred for 20 min at room temperature. A further portion of ammonium formate (128 mg, 2.03 mmol) was then added. Stirring was maintained overnight. The reaction mixture was filtered to remove catalyst and concentrated to dryness. The residue was purified by flashmaster column eluting with a gradient elution (DCM→DCM:MeOH 98:2) to afford pure 1,9-diaminoacridine as a brown-yellow solid (57 mg, 40%). $^1$H NMR and LCMS analyses conformed to structure.

Example 6

Attachment of Acridine Dye to Peptide

To facilitate the attachment of fluorophores to peptides and proteins, carboxylic acid derivatives of the fluorophore are often generated, as such compounds will react with an amino functionality on peptides and proteins to afford labelling through amide bond formation.

An initial target molecule:

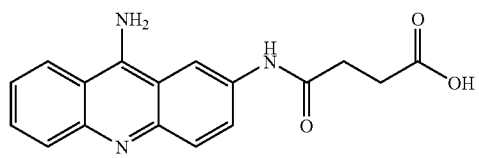 [SMILES: Nc1c2ccccc2nc2ccc(NC(=O)CCC(=O)O)cc12]

was selected which contained a carboxylic acid moiety at the 3-position that would enable attachment to a peptide via an amide bond linkage. [Note: the carboxylic acid functionality is attached to the aromatic ring of 9-aminoacridine via an amide bond bridge at the 3-position].

However, a resin based approach was developed for synthesis of dye-labelled peptides which did not require generation of the above target molecule but led to the same dye linked biomolecule. The resin bound substrate was first reacted with glutaric anhydride and then coupled to 3,9-diaminoacridine (a non-fluorescent precursor compound). Cleavage of the resin bound material furnished the desired 9-aminoacridine labelled peptide substrate (Scheme 1).

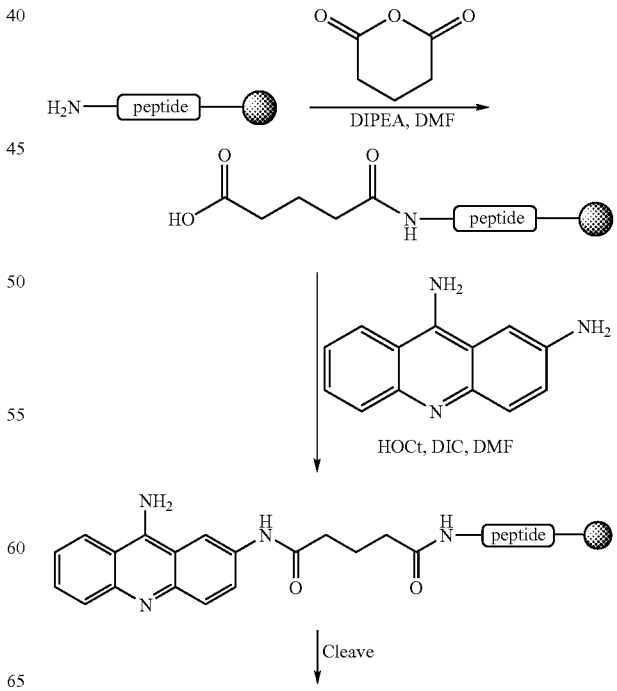

-continued

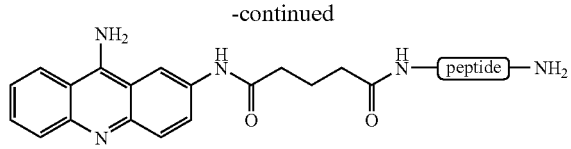

Step 1: Couple Glutaric Anhydride

A solution of glutaric anhydride (11 mg, 0.1 mmol) and diisopropylethylamine (40 ul, 0.2 mmol) in DMF (0.5 ml) was added to the resin (250 mg). The mixture was sonicated for 3 hours and then washed with DMF and DCM. A ninhydrin test indicated that the coupling reaction was complete.

Step 2: Couple 3,9-Diaminoacridine

A solution of DIC (200 ul, 0.5M in DMF) and HOCt (200 ul, 0.5M in DMF) was added to the resin and the mixture was sonicated for 15 minutes. A solution of 3,9-diaminoacridine (10 mg, 0.05 mmol) in DMF (0.5 ml) was added to the resin mixture and sonication continued overnight. The resin was washed with DMF, DCM and ether.

Step 3: Cleavage

Dry resin was treated with a solution of TFA:TIS:water (95:2.5:2.5, 3 ml) with stirring for 3 hours. The solution was then filtered into cold ether and the precipitated peptide was centrifuged, washed with ether and lyophilised to give a fluffy solid. Preparative HPLC furnished the desired compound.

Example 7

Fluorescence Analysis of a Series of 9-Aminoacridine Derivatives, Derivatised at Combinations of the 2, 3 and 6 Positions with Amino and/or Acetamidyl Functionalities As a starting point for the acetamidyl-9-aminoacridine derivatives, the 3-acetamidyl-9-aminoacridine was studied and shown to have a similar fluorescence lifetime and fluorescence intensity (FIG. 5) to the 9-aminoacridine attached to a peptide via an amide at position 3. [3-Acetamidyl-9-aminoacridine lifetime is 17 ns and 9-aminoacridine-3-DEVDSK lifetime is 18 ns].

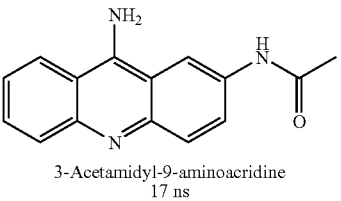

3-Acetamidyl-9-aminoacridine
17 ns

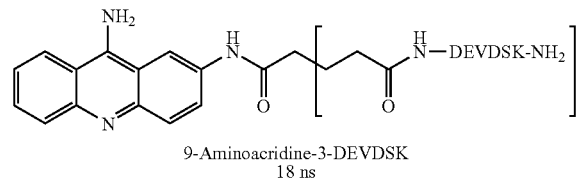

9-Aminoacridine-3-DEVDSK
18 ns

The series of acetamidyl-9-aminoacridine derivatives was then analysed (FIGS. 6a, 6b and Table 2). The free dye systems (with no acetylation to mimic the unbound dye) were also studied but were shown to be very poorly fluorescent.

The results indicate that although the fluorescence intensity is compromised on functionalisation of the 9-aminoacridine ring, an increase in fluorescence lifetime is observed.

TABLE 2

| Number | Compound | Lifetime (ns) | Relative intensity Ex405 nm, $Em_{max}$ |
|---|---|---|---|
| 1 | 9-Aminoacridine | 15 | 1 |
| 2 | 2-Acetamidyl-9-aminoacridine | 15 | 0.5 |
| 2 | 2-Acetamidyl-9-aminoacridine | 15 | 1.4* |
| 3 | 3-Acetamidyl-9-aminoacridine | 17 | 0.625 |

TABLE 2-continued

| Number | Compound | Lifetime (ns) | Relative intensity Ex405 nm, Em$_{max}$ |
|---|---|---|---|
| 4 | 3,6-Diacetamidyl-9-aminoacridine | 20 ns | 0.25 |
| 5 | 2,9-Diaminoacridine | multiexponential | 0.125 |
| 6 | 3,9-Diaminoacridine | Not fluorescent | Not fluorescent |
| 7 | 3-Acetamidyl-6,9-diaminoacridine | multiexponential | Not fluorescent |

(*Ex340 nm)

In addition, on excitation of 2-acetamidyl-9-aminoacridine (2) at 340 nm an increase in the fluorescence intensity was observed resulting in a response that was more intensely fluorescent than 9-aminoacridine.

Example 8

Fluorescence Lifetime Based Caspase-3 Assay using Peptides Labelled with 3,9-diaminoacridine Using the method described in example 6, the dye was coupled to two peptides, DEVDSK and DEVDSW and the fluorescence properties were measured (FIG. 7). The lysine (K) containing peptide was shown to be fluorescent whereas the fluorescence intensity of the tryptophan (W) containing peptide was quenched by 85%. Tryptophan was also shown to have an effect on the fluorescence lifetime of the acridine dye, as the lifetime changed significantly from 18 ns (DEVDSK) to 7 ns (DEVDSW). Consequently, tryptophan was shown to be a quencher for 9-aminoacridine fluorescence intensity and a modulator of its fluorescence lifetime.

The two peptide sequences were selected as they contain the sequence DEVDS which is a substrate for the enzyme Caspase-3, and it was anticipated that an enzyme mediated cleavage of the tryptophan quenched substrate, 9-aminoacridine-3-DEVDSW, would produce a fluorescence intensity change (increase) and a change in the fluorescence lifetime (increase) (Scheme 2), thus enabling the dye to be employed as a fluorescent reporter in biochemical and cell based assays.

Scheme 2

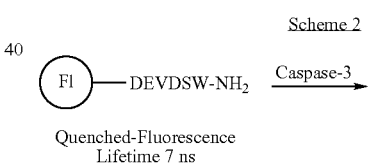

Quenched-Fluorescence
Lifetime 7 ns

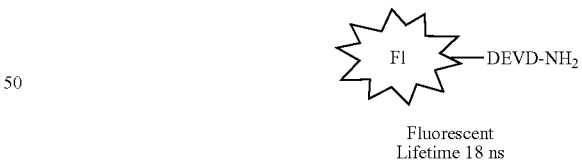

Fluorescent
Lifetime 18 ns

Caspase 3 Mediated Cleavage of Acridine-DEVDSW

The 9-aminoacridine labelled peptide substrate, AA-DEVDSW (1 uM concentration in 10 mM HEPES buffer pH 7.4 containing 10% sucrose, 0.1% CHAPS, 100 mM NaCl, 1 mM EDTA, 10 mM DTT) was employed in a biochemical assay using Caspase-3 recombinant enzyme (50 U and 20 U) at 30° C. The assay mixture was analysed at time intervals using an Edinburgh Instruments Fluorescence Lifetime Plate Reader. During the progress of the reaction a change in fluorescence lifetime of the reaction mixture was observed (from 9 ns to 17 ns) indicating that the substrate was being converted to product. The data could also be easily viewed as a change in percentage cleavage over time, confirming that the reaction was progressing to completion after 90 minutes when 50 units of caspase 3 was employed (see FIGS. 8 and 9).

Example 9

Synthesis of 3-(9-amino-acridin-2-yl)-propionic acid (1) Target 1: 3-(9-amino-acridin-2-yl)-propionic acid To facilitate the attachment of fluorophores to peptides and proteins, carboxylic acid derivatives of the fluorophore are often generated, as such compounds will react with an amino functionality on peptides and proteins to afford labelling through amide bond formation. 3-(9-aminoacridin-2-yl)-propionic acid (Target 1) was selected which contained a carboxylic acid moiety at the 3-position that would enable attachment to a peptide via an amide bond linkage. [Note: the carboxylic acid functionality is attached to the aromatic ring of 9-aminoacridine via a methylene spacer as it was envisaged that such a linker would maintain the attractive fluorescence properties of the core 9-aminoacridine fluorophore].

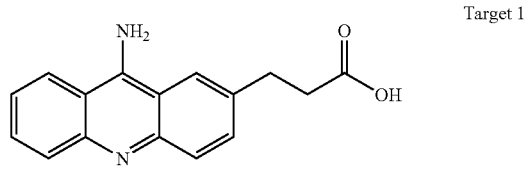 [SMILES: Nc1c2ccccc2nc2ccc(CCC(=O)O)cc12]

Target 1

Step 1:
Synthesis of 4'-bromodiphenylamine-2-carboxylic acid 3 by Ullman reaction of 2-chlorobenzoic acid 1 and 4-bromoaniline 2.

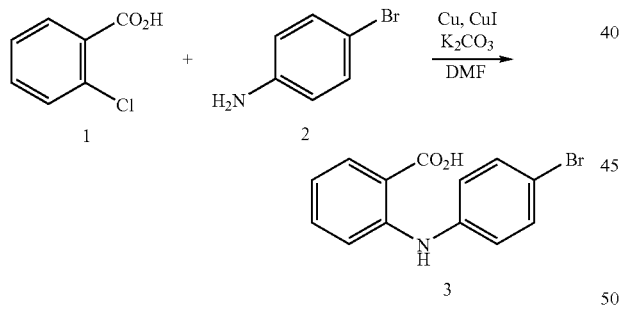

Charges:

| Reagent | MWt | Wt | Vol | mmol | Equivalent |
|---|---|---|---|---|---|
| 2-Chlorobenzoic acid | 156.57 | 1 g | — | 6.39 | 1 |
| 4-Bromoaniline | 172.03 | 1.15 g | — | 6.71 | 1.05 |
| Copper powder | 63.55 | 80 mg | — | — | Catalytic |
| Copper (I) iodide | 190.45 | — | — | — | Catalytic |
| Potassium carbonate | 138.21 | 883 mg | — | 6.39 | 1 |
| Anhydrous DMF | — | — | 6 mL | — | — |

Procedure
2-Chlorobenzoic acid 1 (1 g, 6.39 mmol), 4-bromoaniline 2 (1.15 g, 6.71 mmol) and anhydrous DMF (6 mL) were charged to a 50 mL rbf equipped with a reflux condenser and nitrogen bubbler. To the resulting mixture was added anhydrous potassium carbonate (883 mg, 6.39 mmol) followed by copper powder (80 mg) and a trace of copper (I) iodide. The reaction mixture was heated to 140° C. for 5 hours, and then cooled to room temperature. The suspension was poured onto a mixture of ice/water, acidified with aqueous 0.1M hydrochloric acid solution until pH 4 was reached. The resulting solid was filtered, washed with an excess of water and allowed to air dry for 1 hour. The product was obtained as a green powdery solid (1.67 g). Purification by dry chromatography using a gradient elution (DCM→DCM:MeOH 99:1) followed by slurring in hexane/DCM afforded pure 4'-bromodiphenylamine-2-carboxylic acid 3 as a cream solid (430 mg, 23%). Analyses by $^1$H NMR and LCMS conformed to structure.

Step 2
Cyclisation of 4'-bromodiphenylamine-2-carboxylic acid 3 using $POCl_3$ afforded the corresponding 9-chloroacridine 4.

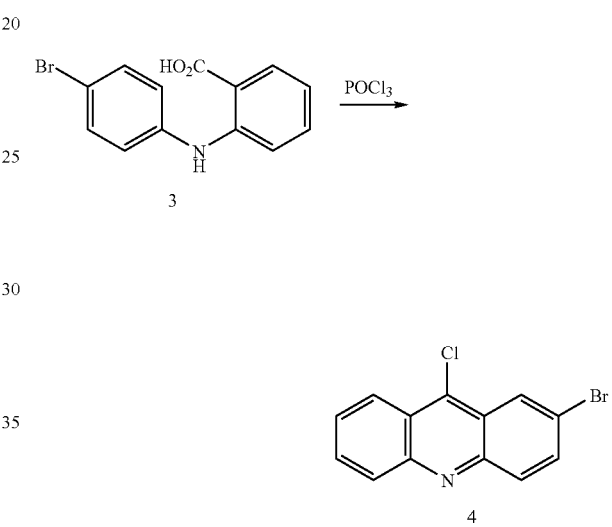

Charges:

| Reagent | MWt | Wt | Vol | mmol | Equivalent |
|---|---|---|---|---|---|
| 4'-Bromodiphenylamine-2-carboxylic acid | 292.13 | 430 mg | — | 1.47 | 1 |
| Phosphorus oxychloride | 153.33 | — | 5 mL | — | — |

Procedure
4'-Bromodiphenylamine-2-carboxylic acid 3 (430 mg, 1.47 mmol) and phosphorus oxychloride (5 mL) were charged to a 25 mL rbf equipped with a reflux condenser and nitrogen bubbler. The reaction mixture was refluxed at 140° C. for 1 hour until a red colour was obtained. The excess $POCl_3$ was removed in vacuo. The reaction mixture was carefully quenched with ice, basified with concentrated aqueous ammonia solution (the flask was kept cold with an ice bath), and extracted with chloroform. The combined organic layers were dried over magnesium sulphate, filtered and concentrated to yield the crude product. Purification by dry chromatography using a gradient elution (Hexane e Hexane:EtOAc 96:4) afforded pure 3-bromo-9-chloroacridine 4 as a cream solid (397 mg, 92%). Analyses by $^1$H NMR and LCMS conformed to structure.

Step 3

Synthesis of 3-bromo-9-aminoacridine 5 by amination using phenol and ammonium carbonate.

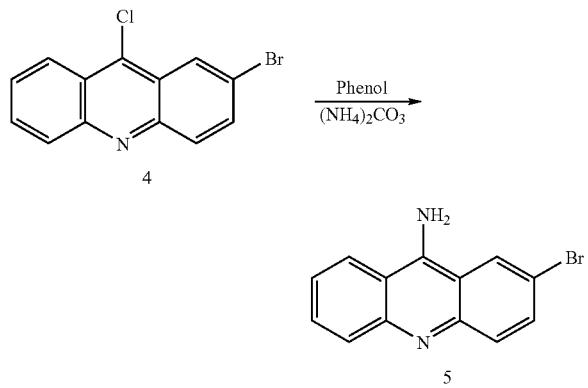

Charges:

| Reagent | MWt | Wt | mmol | Equivalent |
| --- | --- | --- | --- | --- |
| 3-Bromo-9-chloroacridine | 292.56 | 397 mg | 1.36 | 1 |
| Phenol | 94.11 | 1.31 g | 14.01 | 10.3 |
| Ammonium carbonate | 96.09 | 200 mg | 2.04 | 1.5 |

Procedure

To a 25 mL rbf equipped with a reflux condenser and nitrogen bubbler were charged 3-bromo-9-chloroacridine 4 (397 mg, 1.36 mmol) and phenol (1.31 g, 14.01 mmol). The mixture was heated to 70° C. Stirring was continued and powdered ammonium carbonate (200 mg, 2.04 mmol) was added as rapidly as the vigorous effervescence permitted. The temperature was quickly raised to 120° C. and the reaction mixture was stirred at this temperature for a further 1 hour. After cooling to 30° C., acetone (3.6 mL) was added and the flask was cooled to 0° C. for 2 hours to precipitate 9-aminoacridine hydrochloride. The suspension was filtered and washed free from phenol with acetone. The product HCl salt was obtained as a yellow solid (415 mg). The solid was slurried in aqueous 0.1M sodium hydroxide solution, filtered and washed with water. 3-Bromo-9-aminoacridine 5 was obtained as a yellow solid (275 mg, 74%). ¹H NMR and LCMS analyses conformed to structure.

Step 4

Heck reaction with tert-butyl acrylate yielded 3-(9-amino-acridin-2-yl)-acrylic acid tert-butyl ester 6.

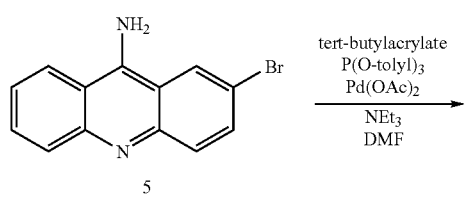

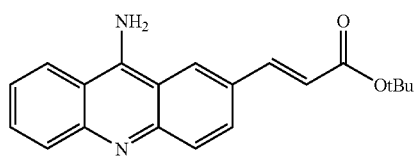

Charges:

| Reagent | MWt | Wt | Vol | mmol | Equivalent |
| --- | --- | --- | --- | --- | --- |
| 3-Bromo-9-aminoacridine | 273.13 | 120 mg | — | 0.44 | 1 |
| tert-Butyl acrylate | 128.17 | — | 75 μL | 0.48 | 1.1 |
| Tri-(O-Tolyl)phosphine | 304.38 | 25 mg | — | 0.08 | 0.18 |
| Palladium (II) acetate | 224.49 | 6 mg | — | 0.03 | 0.06 |
| Triethylamine | 101.19 | — | 185 μL | 1.32 | 3 |
| Anhydrous DMF | — | — | 1 mL | — | — |

Procedure

To a 10 mL rbf equipped with a nitrogen bubbler were charged 3-bromo-9-aminoacridine 5 (120 mg, 0.44 mmol), tert-butyl acrylate (75 μL, 0.48 mmol) and anhydrous DMF (1 mL). Tri-(O-tolyl)phosphine (25 mg, 0.08 mmol) and palladium (II) acetate (6 mg, 0.03 mmol) were added. The reaction mixture was stirred at room temperature and degassed by applying nitrogen flow and vacuum successively (3 times). The mixture was finally placed under nitrogen atmosphere and triethylamine (185 μL, 1.32 mmol) was added. The red-orange solution was heated to 110° C. for 3 hours and then cooled to room temperature. The brown-orange solution was filtered through Celite and washed with ethyl acetate. This organic layer was then washed with water and concentrated in vacuo to give the crude product as an orange oil. Purification by Flashmaster II using a gradient elution (DCM→DCM:MeOH 60:40) afforded pure 3-(9-amino-acridin-2-yl)-acrylic acid tert-butyl ester 6 as an orange solid (75 mg, 53%). ¹H NMR and LCMS analyses conformed to structure.

Step 5

Reduction of the double bond by catalytic hydrogenation afforded 3-(9-amino-acridin-2-yl)-propionic acid tert-butyl ester 7

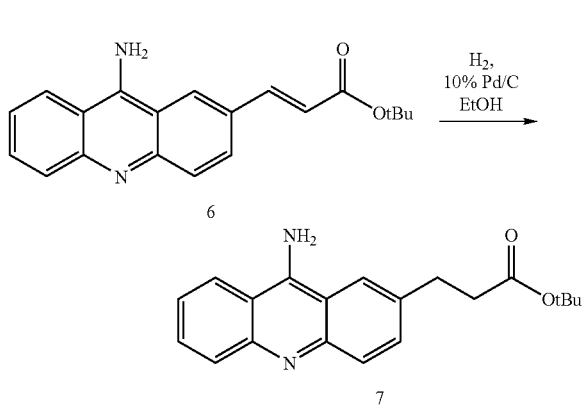

Charges:

| Reagent | MWt | Wt | Vol | mmol | Equivalent |
|---|---|---|---|---|---|
| 3-(9-Amino-acridin-2-yl)-acrylic acid tert-butyl ester | 320.39 | 40 mg | — | 0.12 | 1 |
| 10% Pd/C | — | 15 mg | — | — | Catalytic |
| Ethanol | — | — | 25 mL | — | — |

Procedure 3-(9-Amino-acridin-2-yl)-acrylic acid tert-butyl ester 6 (40 mg, 0.06 mmol) was dissolved in ethanol (25 mL). 10% Pd/C (15 mg) was added and the solution was put under hydrogenation at 3 bar for 1 h30. The mixture was filtered through Celite and the solvent was evaporated. The residue was purified by Flashmaster II using a gradient elution (DCM→DCM:MeOH 40:60) afforded pure 3-(9-amino-acridin-2-yl)-propionic acid tert-butyl ester 7 as an orange oil (20 mg, 52%). $^1$H NMR and LCMS analyses conformed to structure.

Step 6

Cleavage of the tert-butyl ester with TFA yielded Target 1.

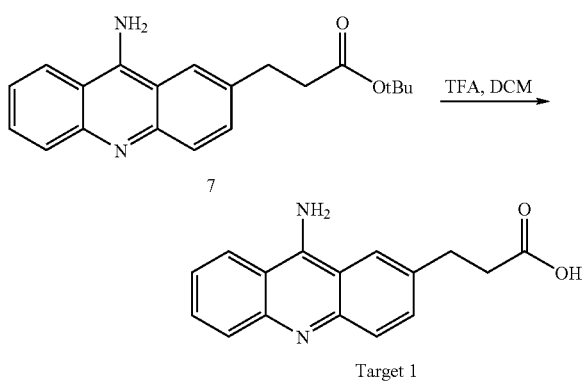

Charges:

| Reagent | MWt | Wt | Vol | mmol |
|---|---|---|---|---|
| 3-(9-Amino-acridin-2-yl)-propionic acid tert-butyl ester | 322.41 | 55 mg | — | 0.17 |
| Trifluoroacetic acid | — | — | 2 mL | — |
| Anhydrous dichloromethane | — | — | 2 mL | — |

Procedure 3-(9-Amino-acridin-2-yl)-propionic acid tert-butyl ester 7 (55 mg, 0.17 mmol) was dissolved in anhydrous dichloromethane (2 mL) and trifluoroacetic acid (2 mL) was carefully added. The mixture was stirred at room temperature overnight before evaporation of the solvent. Co-evaporation with diethyl ether (3 times) afforded a yellow solid, which was slurried in diethyl ether, filtered and washed with diethyl ether. Pure 3-(9-amino-acridin-2-yl)-propionic acid (Target 1) was isolated as a yellow TFA salt (49 mg, 76%). $^1$H NMR and LCMS analyses conformed to structure.

2. Synthetic Route to Afford 3-(9-aminoacridin-2-yl)-propionic acid (Target 1)

The chemistry shown in scheme 3 worked well to successfully synthesise 3-(9-amino-acridin-2-yl)-propionic acid as TFA salt.

Ullmann reaction (Step 1) of 2-chlorobenzoic acid 1 and 4-bromoaniline 2 afforded 4'-bromodiphenylamine-2-carboxylic acid 3. Cyclisation with POCl$_3$ followed by amination gave the expected 3-bromo-9-aminoacridine 5 in good yield and purity.

Heck reaction with tert-butyl acrylate (Step 4) worked well to successfully synthesise 3-(9-amino-acridin-2-yl)-acrylic acid tert-butyl ester (Compound 6). The best condition to reduce the double bond was a catalytic hydrogenation at 3 bars in ethanol. The expected 3-(9-amino-acridin-2-yl)-propionic acid tert-butyl ester (Compound 7) was isolated by column chromatography as the major product. Another isomer and a by-product resulting in the reduction of the aromatic ring were also isolated.

Finally, deprotection of the tert-butyl ester with TFA yielded 3-(9-amino-acridin-2-yL)-propionic acid as a TFA salt. LCMS and NMR conformed to structure. Purity >95%.

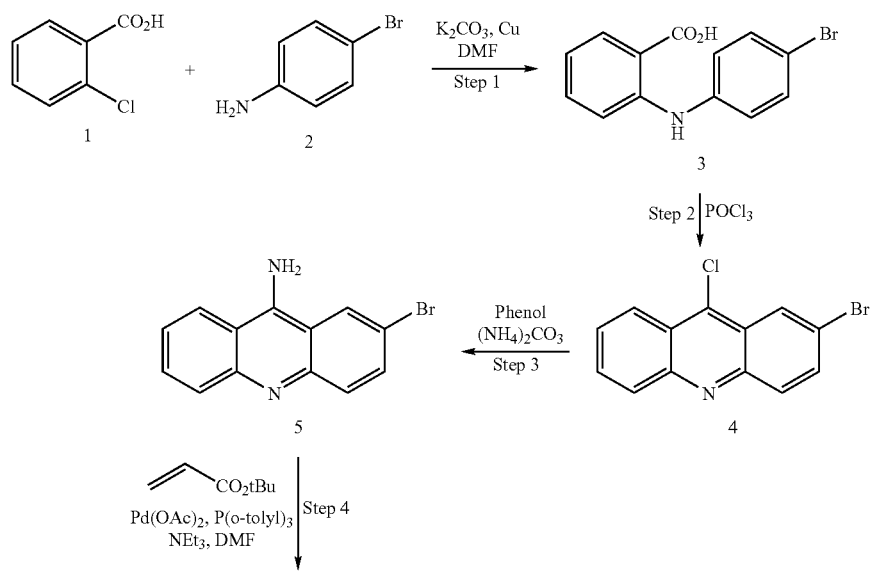

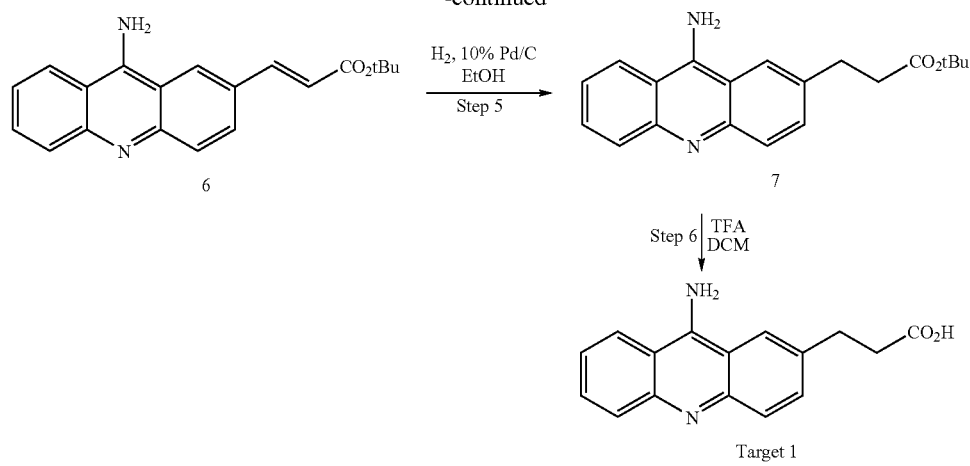

The fluorescence emission spectra of 3-(9-amino-acridin-2-yl)-propionic acid and 3-(9-amino-acridin-2-yl)-propionic acid tertiary butyl ester were compared to 9-aminoacridine (FIG. 10). The fluorescence lifetimes of these and other related compounds were also measured (Table 3). The fluorescence properties were found to be comparable to the parent 9-aminoacridine.

Example 10

Synthesis of Dye Labelled Peptide using 3-(9-aminoacridin-2-yl)-propionic acid

Synthesis Procedures

Step 1: Attachment of 3-(9-Amino-acridin-2-yl)-propionic acid to a peptide 3-(9-Amino-acridin-2-yl)-propionic acid (10 mg, 0.03 mmol) was dissolved in DIC (60 ul, 0.5M in DMF) and HOCt (60 ul, 0.5M in DMF) and the solution was sonicated for 15 minutes. The solution was then added to the resin (100 mg) and sonication continued for 5 hours. The resin was washed with DMF, DCM and ether.

Step 2: Cleavage of Peptide Substrate from Resin

Dry resin was treated with a solution of TFA:TIS:water (95:2.5:2.5, 3 ml) with stirring for 3 hours. The solution was then filtered into cold ether and the precipitated peptide was centrifuged, washed with ether and lyophilised to give a fluffy solid. Preparative HPLC furnished the desired compound.

Synthesis of Peptide Substrates for Caspase 3 Assay

Two target dye labelled peptide substrates were proposed, 3-(9-Aminoacridin-2-yl) propionyl-DEVDSK and 3-(9-Aminoacridin-2-yl) propionyl-DEVDSW. The two substrates were synthesised and the fluorescence intensity and lifetime properties were analysed.

The 3-(9-amino-acridin-2-yl) propionic acid was coupled directly to the peptide resin using HOCt and DIC in DMF and then the peptide was cleaved from the resin to give the target dye-labelled peptide substrate (Scheme 5). This procedure was followed for the synthesis of both peptide products, DEVDSK and DEVDSW.

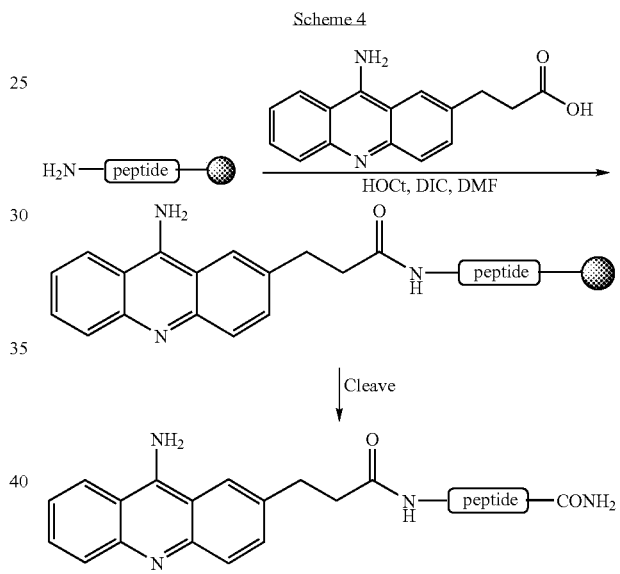

Scheme 4

The fluorescence intensity of the labelled peptides was measured and compared to free 9-aminoacridine and it was shown that the lysine derivative (DEVDSK) had a comparable emission spectrum and fluorescence intensity to that of 9-aminoacridine (FIG. 11). In addition, it was confirmed that tryptophan was an efficient quencher of the fluorescence intensity of the acridine dye and in this particular case tryptophan quenched the dye molecule by 75% (FIG. 11).

The fluorescence lifetime properties were also very encouraging, the presence of tryptophan in the dye-labelled peptide substrate resulted in a decrease in fluorescence lifetime from 17.7 ns to 7.6 ns (FIG. 12 and Table 3).

Example 11

Caspase-3 Mediated Cleavage of 3-(9-amino acridin-2-yl) propionyl-DEVDSW

Caspase 3 Enzyme Assay
Solutions
Buffer: 20 mM HEPES buffer pH7.4 containing 10% sucrose, 0.1% CHAPS, 100 mM NaCl, 1 mM EDTA, 10 mM DTT Substrate solution: 10 uM 3-(9-aminoacridin-2-yl) propionyl-DEVDSW in buffer.
Product solution: 10 uM 3-(9-aminoacridin-2-yl) propionyl-DEVDSK in buffer.
Enzyme solution: 10 U/ul in buffer.
Procedure To the well of a 96-well plate was added buffer (88 ul), substrate solution (10 ul, 1 uM final conc.) and enzyme (2 ul for 20 U). Reactions were performed in triplicate and also at varying enzyme concentrations. The reaction progress was followed at time intervals using an Edinburgh Instruments Fluorescence Lifetime Plate Reader against wells containing product and substrate standards.

Caspase 3 Mediated Cleavage of 3-(9-Aminoacridin-2-yl) propionyl-DEVDSW

The partially quenched 9-aminoacridine-labelled peptide substrate, 3-(9-aminoacridin-2-yl) propionyl-DEVDSW, was employed in a biochemical enzymatic cleavage assay using recombinant Caspase-3 enzyme purchased from Calbiochem. The assay was carried out using 1 uM substrate concentration in 20 mM HEPES buffer pH 7.4 containing 10% sucrose, 0.1% CHAPS, 100 mM NaCl, 1 mM EDTA, 10 mM DTT, in the presence of either 20 or 50 units of enzyme (100 ul final volume). The assay mixture was analysed at time intervals using an Edinburgh Instruments Fluorescence Lifetime Plate Reader. During the progress of the reaction a change in fluorescence lifetime of the reaction mixture was observed (from 8.5 ns to 15.5 ns) indicating that the substrate was being converted to product (FIG. 13). The deviation in fluorescence lifetime from that stated above was a consequence of the buffer system.

The data could also be easily viewed as a change in percentage cleavage over time, confirming that the reaction was progressing to completion after 60 minutes when 50 units of caspase 3 enzyme was employed (FIG. 14).

TABLE 3

Fluorescence Lifetime Data Table Of Molecules Synthesised

| Structure | Name | Lifetime* (ns) |
|---|---|---|
| (3-Bromo-9-aminoacridine structure) | 3-Bromo-9-aminoacridine | 13.0 |
| (9-amino-acridin-2-yl acrylic acid tert-butyl ester structure) | 3-(9-Amino-acridin-2-yl)-acrylic acid tert-butyl ester | 11.2 |
| (9-amino-acridin-2-yl propionic acid butyl ester structure) | 3-(9-Amino-acridin-2-yl)-propionic acid-butyl ester | 16.7 |
| (9-amino-acridin-2-yl propionic acid TFA salt structure) | 3-(9-Amino-acridin-2-yl)-propionic acid as TFA salt | 17.0 |
| (9-amino-acridin-2-yl propionyl-DEVDSK structure) | 3-(9-Amino-acridin-2-yl)-propionyl-DEVDSK | 17.7 |
| (9-amino-acridin-2-yl propionyl-DEVDSW structure) | 3-(9-Amino-acridin-2-yl)-propionyl-DEVDSW | 7.7 |

Example 12

Synthesis of NHS Ester Derivative of 3-(9-aminoacridin-2-yl)-propionic acid [3-(9-aminoacridin-2-yl)-propionic acid 2,5-dioxo-pyrrolidin-1-yl ester]

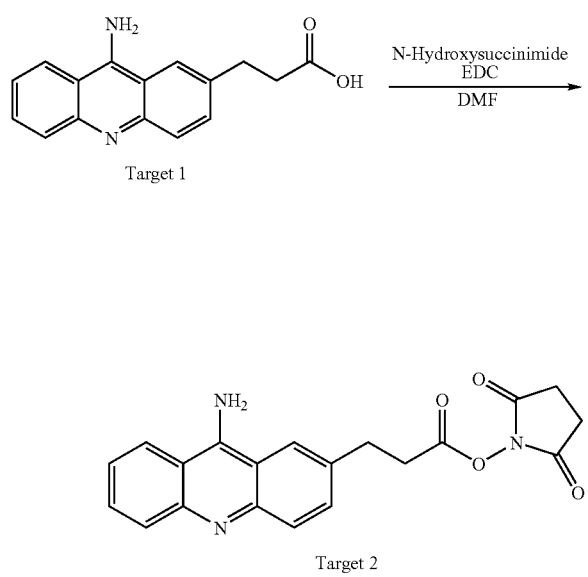

Charges:

| Reagent | MWt | Wt | Vol | mmol | Equivalent |
|---|---|---|---|---|---|
| 3-(9-Amino-acridin-2-yl)-propionic acid as TFA salt | 380.32 | 10 mg | — | 0.03 | 1 |
| N-hydroxysuccinimide | 115.09 | 5 mg | — | 0.04 | 1.3 |
| 1-Ethyl-3-[3-(dimethylamino)-propyl]carbodiimide hydrochloride | 191.71 | 8 mg | — | 0.04 | 1.3 |
| Anhydrous DMF | — | — | 500 μL | — | — |

Procedure 3-(9-Amino-acridin-2-yl)-propionic acid as TFA salt (Target 1) (10 mg, 0.03 mmol), N-hydroxysuccinimide (5 mg, 0.04 mmol) and anhydrous DMF (500 μL) were charged to a 5 mL rbf equipped under a nitrogen atmosphere. The reaction mixture was cooled to 0° C. and 1-ethyl-3-[3-(dimethylamino)-propyl]carbodiimide hydrochloride (8 mg, 0.04 mmol) was added. The yellow solution was stirred at 0° C. for 10 min then at room temperature overnight. After 1 hour, the mixture became an orange solution.

The reaction mixture was partitioned between water and ethyl acetate. The aqueous layer was extracted with ethyl acetate (3 times) and freeze-dried. Crude Target 2 was obtained as a sticky yellow solid (21 mg). LCMS analysis conformed to structure. This product was used for the subsequent amidation without further purification.

Synthetic Route to Afford Target 2

3-(9-amino-acridin-2-yL)-propionic acid was successfully activated as the N-hydroxy succinimidyl ester to afford 3-(9-amino-acridin-2-yl)-propionic acid 2,5-dioxo-pyrrolidin-1-yl ester via a coupling reaction with N-hydroxysuccinimide in the presence of DCC or EDC (Scheme 2). The formation of Target 2 was identified spectroscopically.

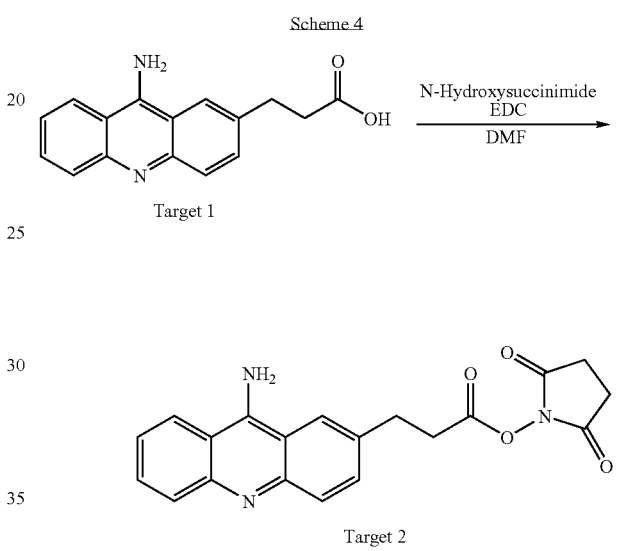

Crude 3-(9-amino-acridin-2-yl)-propionic acid 2,5-dioxo-pyrrolidin-1-yl ester was successfully coupled to benzylamine (1.1 equivalent) in methanol.

The formation of the desired amide was proved by LCMS.

Example 13

Solution Based Coupling of the Dye-NHS Derivative with a Peptide/Protein

The NHS activated 9-aminoacridine compound was coupled to a peptide containing an $N^\alpha$-terminal reactive amine (no other amino functionalities) and to a protein containing several reactive lysine-$N^\epsilon$-amines, in potassium phosphate buffer pH 7.0 as shown in Scheme 5.

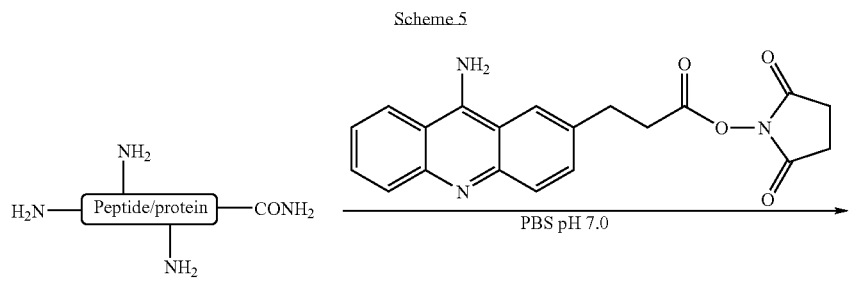

-continued

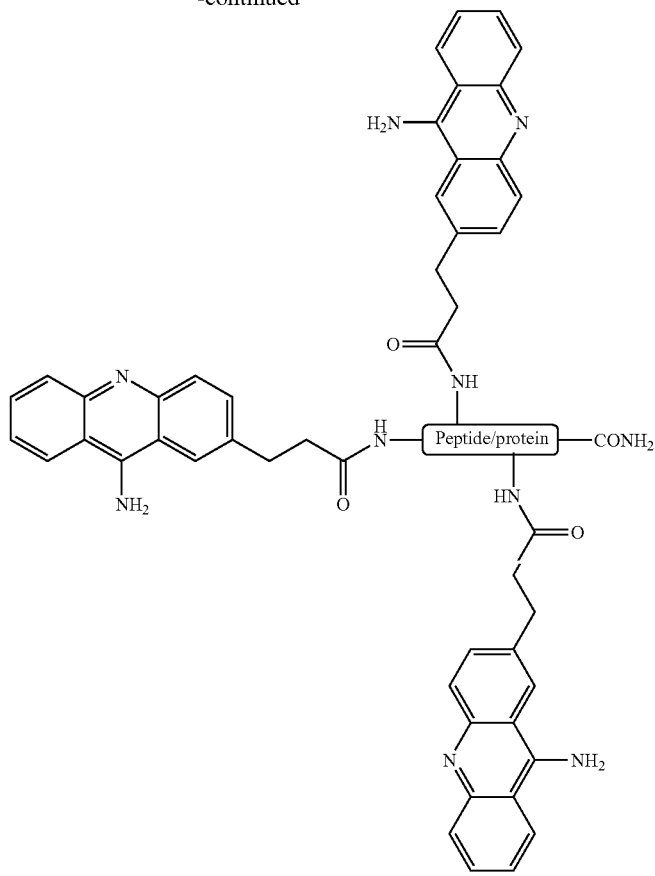

General procedure: The peptide/protein (0.28 umol) was dissolved into 50 mM PBS pH 7.0 (100 ul) and a solution of 3-(9-amino-acridin-2-yl)-propionic acid 2,5-dioxo-pyrrolidin-1-yl ester in DMSO (5 ul, 2.8 umol) was added. The reaction progress was followed by HPLC after 2 hours.

Peptide substrate ($H_2N$-LRRASLG; Mass 770 Da—the peptide substrate contained only one reactive amino group and after 2 hours the reaction had proceeded to >95% completion. This was confirmed by the consumption of the 9-aminoacridine NHS derivative with the formation of a single new peptide product that absorbs at 405 nm and has a mass of 1018.8 Da, which corresponds to the 9-aminoacridine labelled peptide.

Protein substrate (lysozyme; Mass 14308.7)—the protein substrate contained several reactive amino groups and hence the dye labelling could occur randomly at any of these sites. After 2 hours, 90% of protein had become labelled with aminoacridine yielding distinct product of masses, identified by mass spectral analysis, of 14558.8 Da, 14808.3 Da and 15055.3 Da, corresponding to the addition of one, two and three units of 9-aminoacridine respectively.

The Examples described above in relation to synthesis of target molecules and/or coupling of biological molecules should not be considered as limiting. The skilled addressee will easily appreciate how the chemistry can be modified to create different dye molecules and/or dye-biological conjugates.

The invention claimed is:

1. A method for fluorescently labelling a biological molecule, the method comprising:

a) contacting said biological molecule with a dye of formula (I):

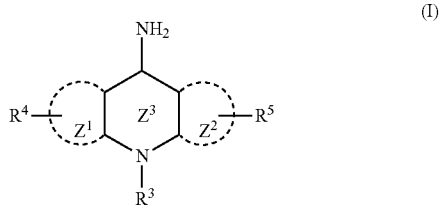

wherein:
the ring $Z^3$ is a pyridyl ring and $R^3$ is absent;
group $R^4$ is attached to an available atom of the $Z^1$ ring structure and group $R^5$ is attached to an available atom of the $Z^2$ ring structure;
$Z^1$ and $Z^2$ independently represent the atoms necessary to complete a benzene ring system which is unsubstituted or substituted; and
$R^4$ and $R^5$ are independently at each occurrence selected from hydrogen, halogen, amide, hydroxyl, cyano, nitro, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, quaternary ammonium and the group -J-K, wherein J is a linker group and K is a reactive group or functional group, and at least one of the groups $R^4$ or $R^5$ is -J-K wherein the linker group contains 1-40 chain atoms comprising carbon, and optionally nitrogen, oxygen, sulphur and/or phosphorus;

wherein the dye of formula (I) is in free or salt form; and b) incubating said dye with said biological molecule under conditions suitable for conjugating said dye to said biological molecule through said reactive group or functional group.

2. A method of measuring the activity of an enzyme on a dye-substrate conjugate, wherein the dye-substrate conjugate comprises (i) at least one dye of formula (I):

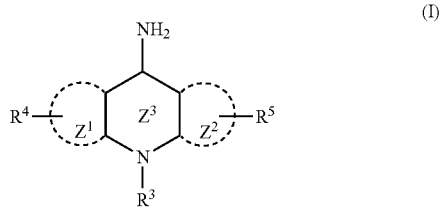

(I)

wherein:

the ring $Z^3$ is a pyridyl ring and $R^3$ is absent;

group $R^4$ is attached to an available atom of the $Z^1$ ring structure and group $R^5$ is attached to an available atom of the $Z^2$ ring structure;

$Z^1$ and $Z^2$ independently represent the atoms necessary to complete a benzene ring system which is unsubstituted or substituted; and $R^4$ and $R^5$ are independently at each occurrence selected from hydrogen, halogen, amide, hydroxyl, cyano, nitro, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, quaternary ammonium and the group -J-K, wherein, J is a linker group and K is a reactive group or functional group and at least one of the groups $R^4$ or $R^5$ is-J-K, wherein the dye of formula (I) is in free or salt form, and (ii) a substrate for the enzyme, wherein said substrate comprises a fluorescence modulating moiety which is capable of being cleaved by the action of the enzyme on the dye-substrate conjugate, resulting in an altered fluorescence lifetime, the method comprising the steps of:

a) measuring the fluorescence lifetime of the dye-substrate conjugate prior to contact with the enzyme;

b) contacting the enzyme with said dye-substrate conjugate, and c) measuring any modulation in fluorescence lifetime as a result of enzyme action on the substrate.

3. The method according to claim 2 wherein the substrate comprises a peptide comprising a tyrosine, tryptophan or phenylalanine as the fluorescence modulating moiety.

4. The method according to claim 3, wherein the peptide comprises 4 to 20 amino acid residues.

5. The method according to claim 2, wherein said enzyme is selected from the group consisting of angiotensin converting enzyme (ACE), caspase, cathepsin D, chymotrypsin, pepsin, subtilisin, proteinase K, elastase, neprilysin, thermolysin, asp-n, matrix metallo protein 1 to 20, papain, plasmin, trypsin, enterokinase and urokinase.

6. The method according to claim 2, wherein the enzyme is selected from the group consisting of protease, esterase, peptidase, amidase, nuclease and glycosidase.

7. A method of screening an effect a test agent has upon the activity of an enzyme, said method comprising the steps of:

a) performing the method of claim 2 in the presence and in the absence of the agent and; and b) determining the activity of said enzyme in the presence and in the absence of the agent;

wherein a difference between the activity of the enzyme in the presence and in the absence of the agent is indicative of the effect of the test agent upon the activity of the enzyme.

8. A method for measuring cellular location and distribution of the dye-substrate conjugate of claim 2, wherein the substrate is capable of being taken up by a living cell, the method comprising the steps of:

a) measuring the fluorescence lifetime of the substrate in a cell-free environment;

b) adding the substrate to one or more cells, and c) measuring the fluorescence lifetime of the substrate following step b);

wherein a modulation in fluorescence lifetime indicates substrate modification and can be used to determine both enzyme activity and localisation.

9. The method of claim 8, wherein said cell is selected from the group consisting of mammalian, plant, insect, fish, avian, bacterial and fungal cells.

10. The method of claim 2 additionally comprising the use of a plurality of different substrates each bound to a plurality of different fluorescent dyes, wherein each of said dye is individually distinguishable from the others by its fluorescence lifetime, thereby enabling simultaneous measurement of a plurality of enzyme activities.

11. A fluorescent dye-biological molecule conjugate comprising a dye covalently bonded to a biological molecule, the dye prior to reaction with the biological molecule having the structure of formula (IV):

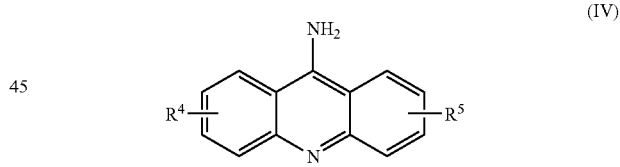

(IV)

wherein $R^4$ and $R^5$ are independently at each occurrence selected from hydrogen, halogen, amide, hydroxyl, cyano, nitro, substituted or unsubstituted alkyl, substituted or unsubstituted alkenyl, substituted or unsubstituted aryl, or heteroaryl substituted or unsubstituted aralkyl, alkyloxy, amino, mono- or di-$C_1$-$C_4$ alkyl-substituted amino, sulphydryl, carbonyl, carboxyl, acrylate, vinyl, styryl, sulphonate, sulphonic acid, quaternary ammonium or the group -J-K; wherein at least one of said $R^4$ or $R^5$ is -JK, wherein J contains 1-40 chain atoms comprising carbon, and optionally nitrogen, oxygen, sulphur and/or phosphorus and, wherein K is prior to reaction with the biological molecule, succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide, hydroxyl, amino, sulphydryl, imidazole, carboxyl, aldehyde, ketone, phosphate and thiophosphate, wherein the biological molecule is linked to the structure of formula (IV)

through said K, and wherein prior to the reaction, the compound of formula (IV) is in free or salt form.

12. The fluorescent dye-biological molecule conjugate according to claim 11 wherein the biological molecule is selected from the group consisting of an antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl including aldehyde and ketone, hydroxyl and carboxyl, phosphate and thiophosphate groups, microbial materials, drugs, hormones, cells, cell membranes and toxins.

13. A kit comprising:
a) a fluorescent dye-biological molecule conjugate according to claim 11; and
b) a binding partner for said biological molecule or enzyme capable of catalytically altering said biological molecule.

14. The method according to claim 2 wherein the fluorescence modulating moiety contains an aromatic system.

15. The method according to claim 1, wherein the dye is a compound of formula (IV):

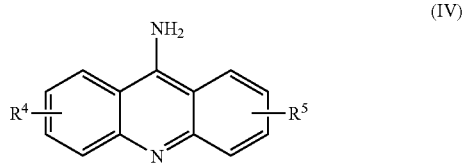

(IV)

in free or salt form, wherein one of $R^4$ and $R^5$ is:
a group -J-K, wherein J contains 1-40 chain atoms comprising carbon, and optionally nitrogen, oxygen, sulphur and/or phosphorus and K is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K is a functional group selected from hydroxyl, amino, sulphydryl, imidazole, carboxyl, carbonyl including aldehyde and ketone, phosphate and thiophosphate; and
the other is hydrogen.

16. The method according to claim 1, wherein the dye is a compound of the following structure:

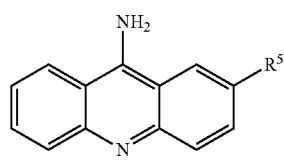

in free or salt form, wherein $R^5$ is a group -J-K, wherein J contains 1-40 chain atoms comprising carbon, and optionally nitrogen, oxygen, sulphur and/or phosphorus and K is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K is a functional group selected from hydroxyl, amino, sulphydryl, imidazole, carboxyl, carbonyl including aldehyde and ketone, phosphate and thiophosphate.

17. The method according to claim 1, wherein the dye is a compound of the following structure:

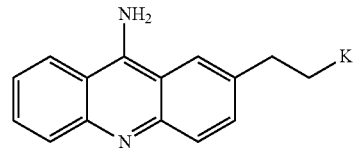

in free or salt form, wherein K is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K is a functional group selected from hydroxyl, amino, sulphydryl, imidazole, carboxyl, carbonyl including aldehyde and ketone, phosphate and thiophosphate.

18. The method according to claim 1, wherein the dye is a compound of the following structure:

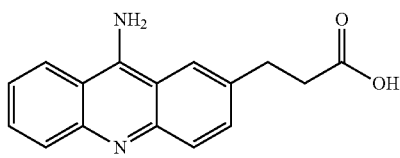 [SMILES: Nc1c2ccccc2nc2ccc(CCC(=O)O)cc12]

in free or salt form.

19. The method according to claim 1, wherein the biological molecule is selected from the group consisting of an antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl including aldehyde and ketone, hydroxyl and carboxyl, phosphate and thiophosphate groups, microbial materials, drugs, hormones, cells, cell membranes and toxins.

20. The method according to claim 2, wherein the dye is a compound of formula (IV):

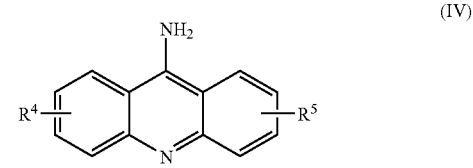

(IV)

in free or salt form, wherein one of $R^4$ and $R^5$ is:
a group -J-K, wherein J contains 1-40 chain atoms comprising carbon, and optionally nitrogen, oxygen, sulphur and/or phosphorus and K is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K is a functional group selected from hydroxyl, amino, sulphydryl, imidazole, carboxyl, carbonyl including aldehyde and ketone, phosphate and thiophosphate; and
the other is hydrogen.

21. The method according to claim 2, wherein the dye is a compound of the following structure:

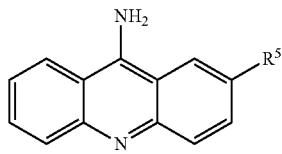

in free or salt form, wherein $R^5$ is a group -J-K, wherein J contains 1-40 chain atoms comprising carbon, and optionally nitrogen, oxygen, sulphur and/or phosphorus and K is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K is a functional group selected from hydroxyl, amino, sulphydryl, imidazole, carboxyl, carbonyl including aldehyde and ketone, phosphate and thiophosphate.

22. The method according to claim 2, wherein the dye is a compound of the following structure:

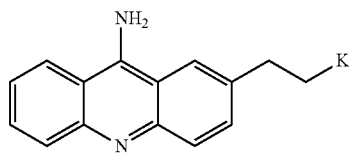

in free or salt form, wherein K is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K is a functional group selected from hydroxyl, amino, sulphydryl, imidazole, carboxyl, carbonyl including aldehyde and ketone, phosphate and thiophosphate.

23. The method according to claim 2, wherein the dye is a compound of the following structure:

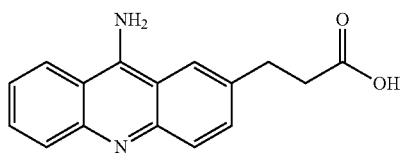 [SMILES: Nc1c2ccccc2nc2ccc(CCC(=O)O)cc12]

in free or salt form.

24. The method according to claim 2, wherein the substrate for the enzyme is selected from the group consisting of an antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl including aldehyde and ketone, hydroxyl and carboxyl, phosphate and thiophosphate groups, microbial materials, drugs, hormones, cells, cell membranes and toxins.

25. The fluorescent dye-biological molecule conjugate according to claim 11, wherein the dye is a compound of formula (IV):

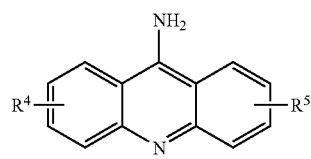

(IV)

in free or salt form, wherein one of $R^4$ and $R^5$ is:
  a group -J-K, wherein J contains 1-40 chain atoms comprising carbon, and optionally nitrogen, oxygen, sulphur and/or phosphorus and K prior to reaction with the biological molecule is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K prior to reaction with the biological molecule is a functional group selected from hydroxyl, amino, sulphydryl, imidazole, carboxyl, carbonyl including aldehyde and ketone, phosphate and thiophosphate; and the other is hydrogen.

26. The fluorescent dye-biological molecule conjugate according to claim 11, wherein the dye is a compound of the following structure:

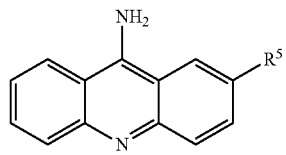

in free or salt form, wherein $R^5$ is a group -J-K, wherein J contains 1-40 chain atoms comprising carbon, and optionally nitrogen, oxygen, sulphur and/or phosphorus and K prior to reaction with the biological molecule is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K prior to reaction with the biological molecule is a functional group selected from hydroxyl, amino, sulphydryl, imidazole, carboxyl, carbonyl including aldehyde and ketone, phosphate and thiophosphate.

27. The fluorescent dye-biological molecule conjugate according to claim 11, wherein the dye is a compound of the following structure:

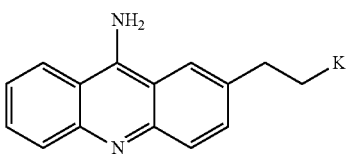

in free or salt form, wherein K prior to reaction with the biological molecule is a reactive group selected from succinimidyl ester, sulpho-succinimidyl ester, isothiocyanate, maleimide, haloacetamide, acid halide, vinylsulphone, dichlorotriazine, carbodimide, hydrazide, phosphoramidiate, pentafluorophylester and alkylhalide or K prior to reaction with the biological molecule is a functional group selected from hydroxyl, amino, sulphydryl, imidazole, carboxyl, carbonyl including aldehyde and ketone, phosphate and thiophosphate.
28. The fluorescent dye-biological molecule conjugate according to claim 11, wherein the dye is a compound of the following structure:
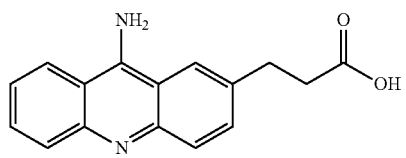 [SMILES: Nc1c2ccccc2nc2ccc(CCC(=O)O)cc12]
in free or salt form.
* * * * *